US012678085B2

(12) United States Patent
Bhagat et al.

(10) Patent No.: US 12,678,085 B2
(45) Date of Patent: *Jul. 14, 2026

(54) HEALTH AND VITAL SIGNS MONITORING PATCH WITH DISPLAY AND MAKING OF SAME

(71) Applicant: Jabil Inc., St. Petersburg, FL (US)

(72) Inventors: Yusuf Abu Tayeb Bhagat, St. Petersburg, FL (US); Girish Satish Wable, St. Petersburg, FL (US); Patrick John Verdon, St. Petersburg, FL (US); Michael Nicholas Arfaras, St. Petersburg, FL (US); Thong Bui, St. Petersburg, FL (US); Krishnaveni Das, St. Petersburg, FL (US); Sai Guruva Reddy Avuthu, St. Petersburg, FL (US); Arnoldo Reta, St. Petersburg, FL (US); Jorg Richstein, St. Petersburg, FL (US)

(73) Assignee: Jabil Inc., St. Petersburg, FL (US)

( * ) Notice: Subject to any disclaimer, the term of this patent is extended or adjusted under 35 U.S.C. 154(b) by 797 days.

This patent is subject to a terminal disclaimer.

(21) Appl. No.: 17/950,211

(22) Filed: Sep. 22, 2022

(65) Prior Publication Data

US 2023/0019660 A1 Jan. 19, 2023

Related U.S. Application Data

(63) Continuation of application No. 16/711,744, filed on Dec. 12, 2019, now Pat. No. 11,478,181.

(51) Int. Cl.
*A61B 5/339* (2021.01)
*A61B 5/00* (2006.01)
(Continued)

(52) U.S. Cl.
CPC .......... *A61B 5/339* (2021.01); *A61B 5/02055* (2013.01); *A61B 5/1117* (2013.01);
(Continued)

(58) Field of Classification Search
CPC ......... A61B 5/339; A61B 5/259; A61B 5/282; A61B 5/02055; A61B 5/1117;
(Continued)

(56) References Cited

U.S. PATENT DOCUMENTS 7,499,739 B2 3/2009 Sweitzer et al.
8,049,406 B2 11/2011 Mackenzie et al.
(Continued)

FOREIGN PATENT DOCUMENTS

EP 3578096 A1 12/2019

OTHER PUBLICATIONS

Lochner et al "All-organic optoelectronic sensor for pulse oximetry," Nature Communications, vol. 5, p. 5745, Dec. 10, 2014.
(Continued)

*Primary Examiner* — Shirley X Jian
(74) *Attorney, Agent, or Firm* — Young Basile Hanlon & MacFarlane, P.C.

(57) ABSTRACT

A vital signs monitoring patch with integrated display (VSM) includes a user access layer for accessing a display section and a first printed silver-silver chloride (Ag—AgCl) electrode. A polyethylene foam layer including battery and plunger cut-outs. A printed circuit board assembly (PCBA) layer including vitals sign monitoring sensors and the battery and connected to the first and second printed Ag—AgCl electrodes. The polyethylene foam layer bonded to the user access layer and the PCBA layer. A sensor layer including reflection mode oximetry components and the second printed Ag—AgCl electrode. A hydrogel conductive adhesive to interact between a user skin and the second printed
(Continued)

Ag—AgCl electrode. A medical tape layer bonded to the user skin and the sensor layer. A plunger connected to the PCBA layer and configured to power on the VSM, where user access of the first printed Ag—AgCl electrode completes a circuit with the second printed Ag—AgCl electrode.

20 Claims, 19 Drawing Sheets

(51) Int. Cl.

| | |
|---|---|
| *A61B 5/0205* | (2006.01) |
| *A61B 5/11* | (2006.01) |
| *A61B 5/145* | (2006.01) |
| *A61B 5/1455* | (2006.01) |
| *A61B 5/259* | (2021.01) |
| *A61B 5/28* | (2021.01) |
| *A61B 5/282* | (2021.01) |

(52) U.S. Cl.
CPC ...... *A61B 5/14539* (2013.01); *A61B 5/14552* (2013.01); *A61B 5/259* (2021.01); *A61B 5/28* (2021.01); *A61B 5/282* (2021.01); *A61B 5/6833* (2013.01); *A61B 5/7445* (2013.01); *A61B 2560/0214* (2013.01); *A61B 2562/0215* (2017.08); *A61B 2562/0219* (2013.01)

(58) Field of Classification Search
CPC ............ A61B 5/14539; A61B 5/14552; A61B 5/6833; A61B 5/7445; A61B 2562/0215; A61B 2560/0214; A61B 2562/0219
See application file for complete search history.

(56) References Cited

U.S. PATENT DOCUMENTS

| | | | |
|---|---|---|---|
| 8,750,954 B2 | 6/2014 | Petersen et al. | |
| 9,782,132 B2 * | 10/2017 | Golda | A61B 5/0002 |
| 9,861,280 B2 * | 1/2018 | Lee | A61B 5/6804 |
| 9,861,314 B2 | 1/2018 | Haverinen et al. | |
| 9,872,525 B2 * | 1/2018 | Lee | A61B 5/01 |
| D811,260 S | 2/2018 | Koskinen | |
| 10,918,289 B1 * | 2/2021 | Wasson | A61B 5/0022 |
| 10,959,678 B2 * | 3/2021 | Golda | A61B 5/0059 |
| 10,971,938 B2 * | 4/2021 | Park | A61B 5/282 |
| 10,973,424 B2 * | 4/2021 | Lee | H01M 10/0431 |
| 11,090,003 B2 * | 8/2021 | Zhao | A61B 5/14542 |
| 11,160,504 B2 * | 11/2021 | Yun | A61B 5/6843 |
| 11,183,303 B2 * | 11/2021 | Matichuk | G16H 50/20 |
| 11,185,284 B2 * | 11/2021 | Aliamiri | A61B 5/0006 |
| 11,229,370 B2 * | 1/2022 | Burg | A61B 5/7246 |
| 11,389,652 B2 * | 7/2022 | Toth | A43B 7/146 |
| 11,478,181 B2 * | 10/2022 | Bhagat | A61B 5/28 |
| 11,510,619 B2 * | 11/2022 | Bhagat | A61B 5/6826 |
| 11,596,779 B2 * | 3/2023 | Tong | A61M 35/10 |
| 11,660,005 B1 * | 5/2023 | Bolus | G16H 40/63 |
| | | | 600/301 |

| | | | |
|---|---|---|---|
| 11,980,467 B2 * | 5/2024 | Bhagat | A61B 5/7445 |
| 12,089,960 B2 * | 9/2024 | Bennet | A61B 5/6823 |
| 2002/0026114 A1 * | 2/2002 | Nissila | A61B 5/02438 |
| | | | 600/384 |
| 2007/0100219 A1 * | 5/2007 | Sweitzer | A61B 5/0002 |
| | | | 600/323 |
| 2007/0100666 A1 * | 5/2007 | Stivoric | G05B 1/01 |
| | | | 374/E1.002 |
| 2007/0249946 A1 * | 10/2007 | Kumar | A61B 5/335 |
| | | | 600/515 |
| 2008/0091090 A1 * | 4/2008 | Guillory | A61B 5/6814 |
| | | | 600/301 |
| 2014/0275932 A1 | 9/2014 | Zadig | |
| 2015/0313484 A1 * | 11/2015 | Burg | A61B 5/021 |
| | | | 600/534 |
| 2016/0029911 A1 * | 2/2016 | Lee | A61B 5/02427 |
| | | | 600/407 |
| 2016/0192716 A1 * | 7/2016 | Lee | G06F 1/163 |
| | | | 2/243.1 |
| 2016/0192856 A1 * | 7/2016 | Lee | A61B 5/6802 |
| | | | 600/382 |
| 2016/0317057 A1 * | 11/2016 | Li | A61B 5/6833 |
| 2017/0049336 A1 * | 2/2017 | Hatch | A61B 5/6833 |
| 2017/0071483 A1 * | 3/2017 | Wang | A61B 5/14551 |
| 2017/0156651 A1 | 6/2017 | Arias et al. | |
| 2017/0296088 A1 * | 10/2017 | Choi | A61B 5/742 |
| 2018/0042540 A1 | 2/2018 | Kinnunen et al. | |
| 2018/0078163 A1 * | 3/2018 | Welch | A61B 5/0002 |
| 2018/0301224 A1 * | 10/2018 | Matichuk | G06N 20/00 |
| 2019/0134396 A1 * | 5/2019 | Toth | A61N 1/0456 |
| 2019/0204865 A1 * | 7/2019 | Von Badinski | G02B 19/0061 |
| 2019/0298210 A1 * | 10/2019 | Bennet | A61B 5/0245 |
| 2019/0307400 A1 * | 10/2019 | Zhao | A61B 5/7221 |
| 2020/0205732 A1 * | 7/2020 | Aliamiri | H01R 13/03 |
| 2021/0177353 A1 * | 6/2021 | Bhagat | G09G 3/20 |
| 2021/0236036 A1 * | 8/2021 | Grob | A61B 5/72 |
| 2021/0361164 A1 * | 11/2021 | Bogdan | A61B 5/746 |
| 2022/0361760 A1 * | 11/2022 | Bhagat | A61B 5/6831 |
| 2023/0095971 A1 * | 3/2023 | He | A61B 5/282 |
| | | | 600/301 |

OTHER PUBLICATIONS

Park et al "Real-Time Heart Monitoring System based on Ring-Type Pulse Oximeter Sensor," Journal of Electrical Engineering and Technology, vol. 8, No. 2, p. 376-384, Mar. 2013.

Yokota et al "Ultraflexible organic photonic skin," Science Advances, Apr. 15, 2016.

Khan et al "A flexible organic reflectance oximeter array," PNAS, vol. 115, No. 47, Nov. 7, 2018.

Khan et al "System Design for Organic Pulse Oximeter," Advances in Sensors and Interfaces, IWASI, Aug. 2015.

Khan et al "Supplementary Information for A flexible organic reflectance oximeter array," PNAS, pp. 1-20 https://www.pnas.org/content/suppl/2018/11/06/1813053115.DCSupplemental, retrieved Oct. 2018.

* cited by examiner

3000

3100

3200

3300

13000

15000

Substrate 15100

Electrolyte 15200

Electrochromic Layer 15300

Electrodes 15400

Substrate 15500

15310

15410

Shell
16200

Ligands    16300

Core
16100

HEALTH AND VITAL SIGNS MONITORING PATCH WITH DISPLAY AND MAKING OF SAME

CROSS REFERENCE TO RELATED APPLICATION

This application is a continuation of U.S. patent application Ser. No. 16/711,744, filed on Dec. 12, 2019, the contents of which are incorporated by reference herein.

TECHNICAL FIELD

This disclosure relates to electronics and in particular, a patch for monitoring and displaying health signs, vital signs, and the like.

BACKGROUND

Vital signs monitoring devices are capable of measuring multiple physiologic parameters of a patient. These physiologic parameters may include heart rate, electrocardiogram (ECG) signals, photoplethysmography (PPG) signals, and other like signals and information. The vital sign monitoring devices come in a variety of forms including smart watches, wearable devices, and the like. The use of such devices has become ubiquitous as users become more health conscious. The devices may be used in a variety of settings including medical facilities, home, and work, and while walking, exercising and performing other activities. The devices, however, lack depicting the multi-parametric measurements associated with the multiple sensing modalities on the devices such as ECG, oxygen saturation, temperature and pH, for example. In addition, the devices may be costly, need maintenance, and may be difficult to use or interpret. Consequently, there is a need for an easy to use vital signs monitoring device which may be more suitable and adaptable for a variety of environments.

SUMMARY

Disclosed herein are implementations of health and/or vital signs monitoring patch with integrated display and methods for making the patches or devices.

In implementations, a vital signs monitoring patch with integrated display includes a user access layer configured to have at least access to a display section and a first printed silver-silver chloride electrode, a polyethylene foam layer including at least a cut-out for a power supply, where the polyethylene foam layer is arranged to bond to the user access layer, a printed circuit board assembly (PCBA) layer including at least one vital sign monitoring sensor and the power supply, the PCBA layer is connected to the first printed silver-silver chloride electrode and a second printed silver-silver chloride electrode, where the PCBA layer is arranged to bond to the polyethylene foam layer, a sensor layer including reflection mode oximetry measurement components and the second printed silver-silver chloride electrode, a hydrogel based conductive adhesive configured to contact a user surface area, where the hydrogel based conductive adhesive is configured to interact between the user surface area and the second printed silver-silver chloride electrode, a medical tape layer, where the medical tape layer is configured to bond to the user surface area and the sensor layer, and a plunger arranged to operate within a cut-out on the polyethylene foam layer and connected to the PCBA layer, where the plunger is accessible on the user access layer and configured to power on the vital signs monitoring patch with integrated display via the power supply, and where access of the first printed silver-silver chloride electrode by a user completes a circuit with the second printed silver-silver chloride electrode.

In implementations, a vital signs monitoring patch with integrated display includes a top layer including at least access to a display, a top printed silver-silver chloride electrode and an activation device, a foam layer including at least a cut-out for a power supply and the activation device, where the polyethylene foam layer is arranged to bond to the top layer, a printed circuit board assembly (PCBA) layer having a top surface and a bottom surface, where the top surface including at least an electrocardiogram (ECG) sensor and the power supply, the ECG sensor connected to the first printed silver-silver chloride electrode and a second printed silver-silver chloride electrode, the bottom surface including at least an oximetry sensor and the second printed silver-silver chloride electrode, and the activation device connected to the PCBA layer, a hydrogel based conductive adhesive configured to contact a user skin surface, where the hydrogel based conductive adhesive is configured to interact between a user skin area and the second printed silver-silver chloride electrode, and a contact layer, wherein the contact layer is configured to bond to a user surface area and the bottom surface of the PCBA layer, and where the activation device is configured to power on the vital signs monitoring patch with integrated display via the power supply, and where access of the first printed silver-silver chloride electrode by a user completes a circuit with the second printed silver-silver chloride electrode.

BRIEF DESCRIPTION OF THE DRAWINGS

The disclosure is best understood from the following detailed description when read in conjunction with the accompanying drawings and are incorporated into and thus constitute a part of this specification. It is emphasized that, according to common practice, the various features of the drawings are not to-scale. On the contrary, the dimensions of the various features are arbitrarily expanded or reduced for clarity.

3

Figure 8:
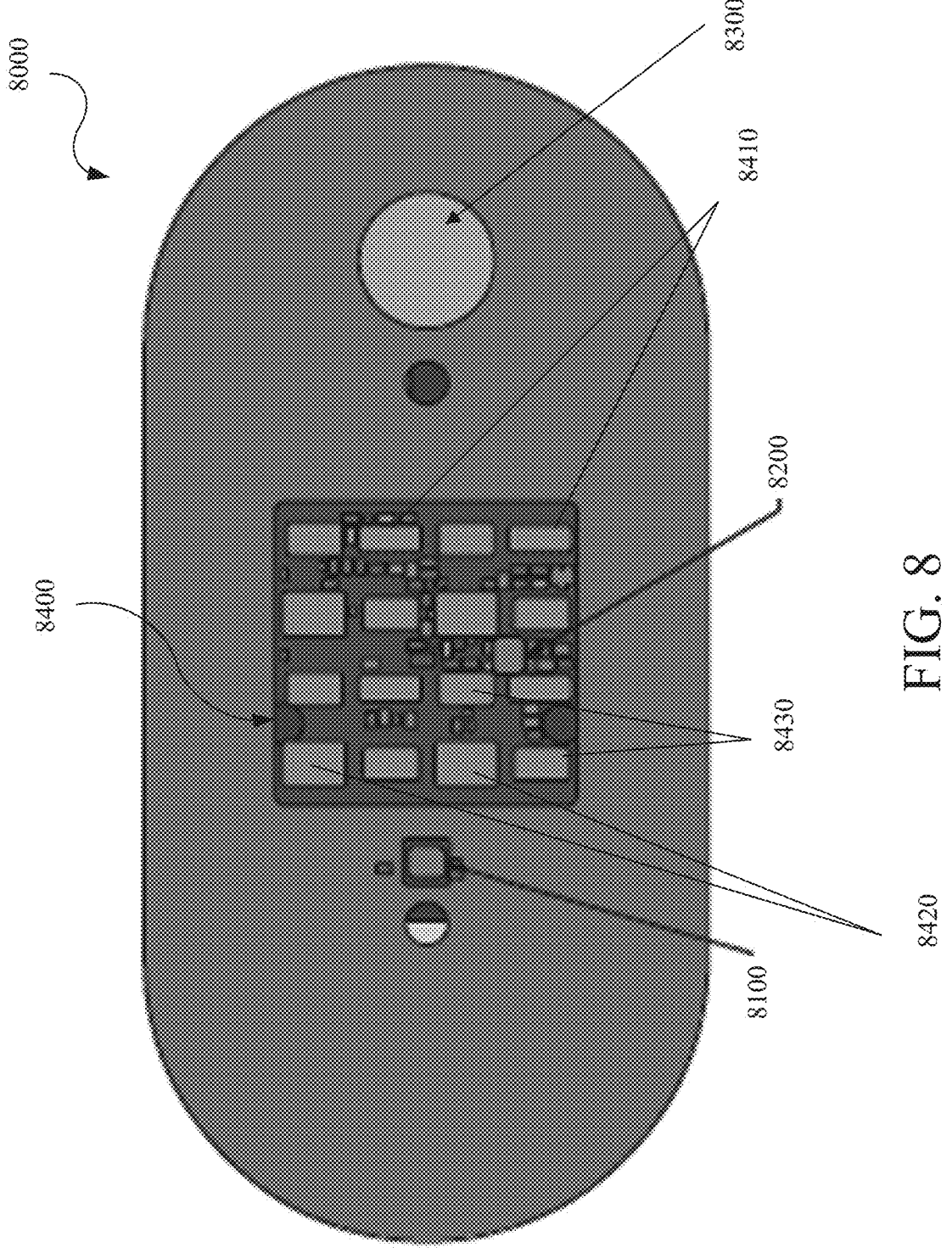
FIG. 8 is a bottom view of a printed circuit board layer of the vital signs monitoring patch with display of FIG. 4 in accordance with certain implementations.
Figure 8A:
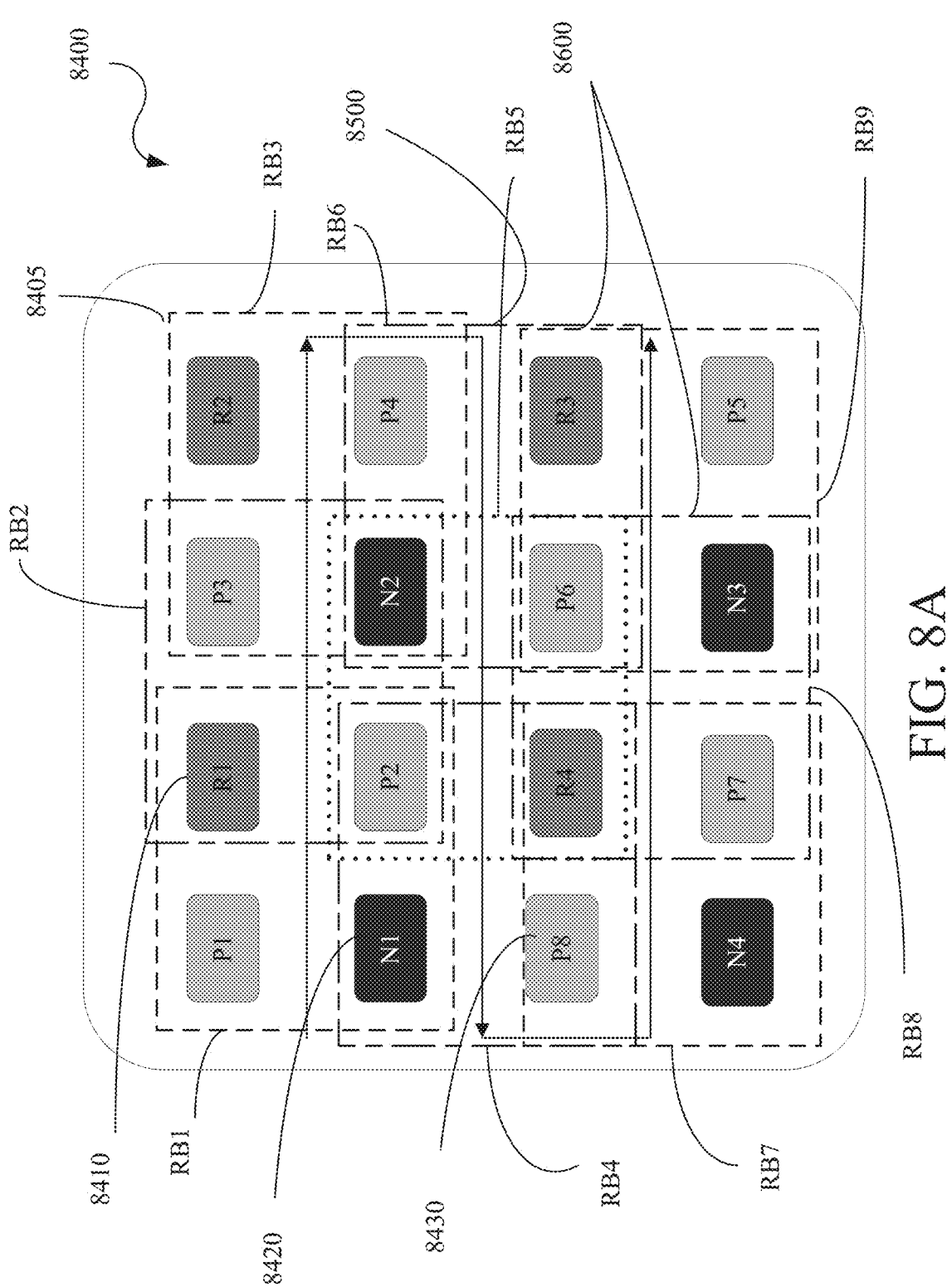

FIG. 8A is a diagram of the reflection mode oximetry measurement components of FIG. 8 in accordance with certain implementations.

Figure 8B:
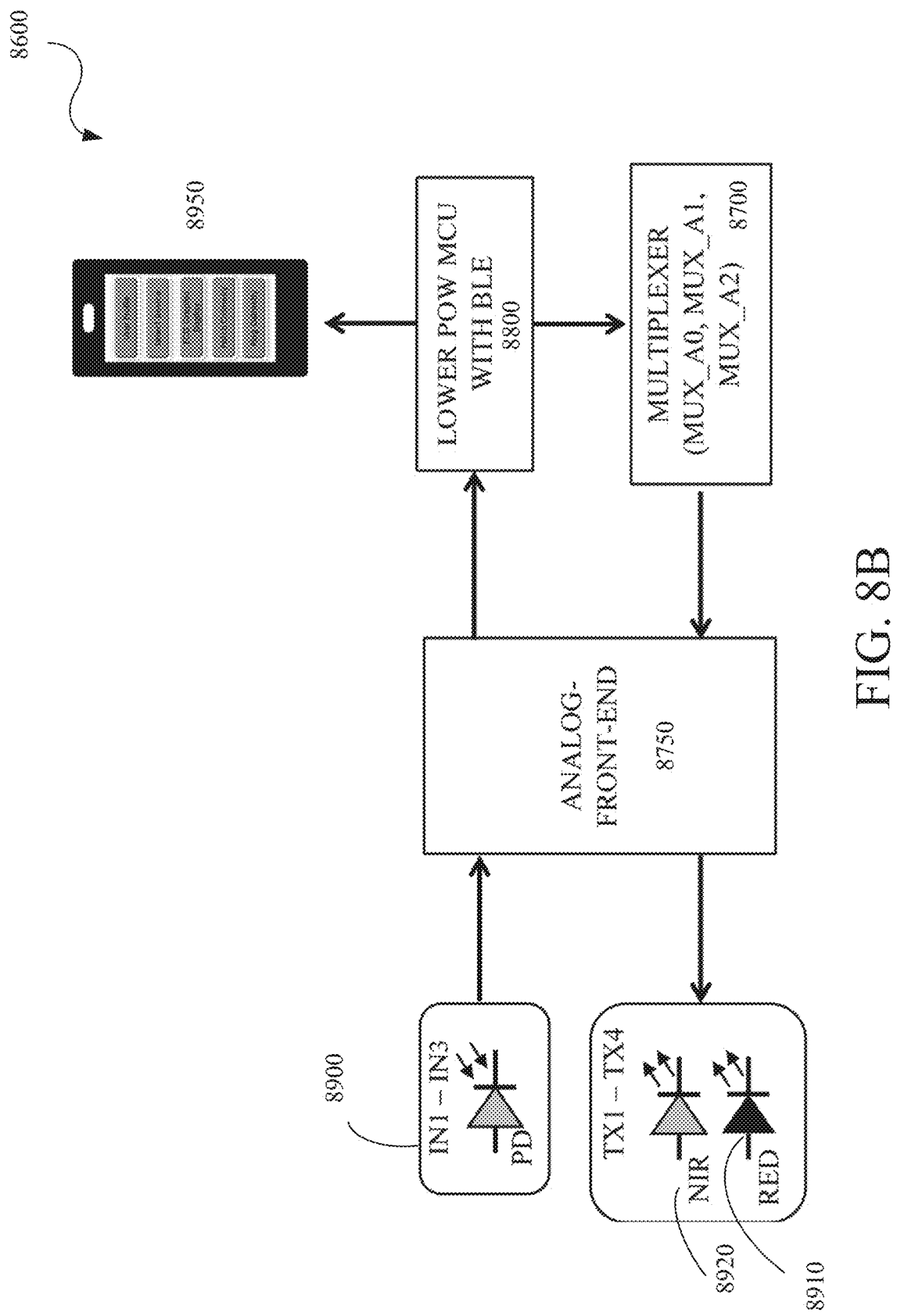

FIG. 8B is a block diagram of a readout circuit for the reflection mode oximetry measurement system of FIG. 8 in accordance with certain implementations.

Figure 9:
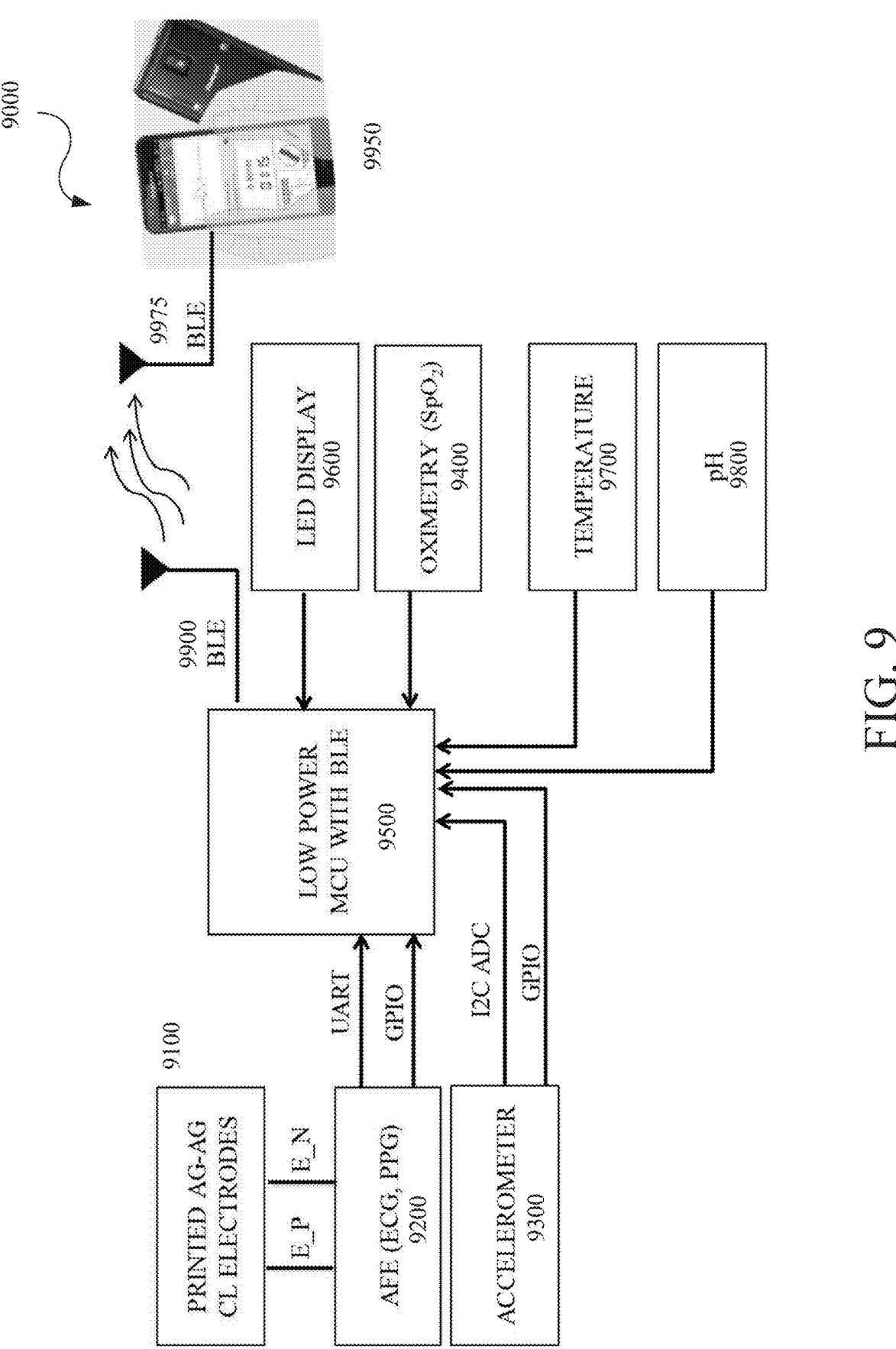

FIG. 9 is an example diagram of a hardware architecture of a vital signs monitoring patch with display in accordance with certain implementations.

Figure 10:
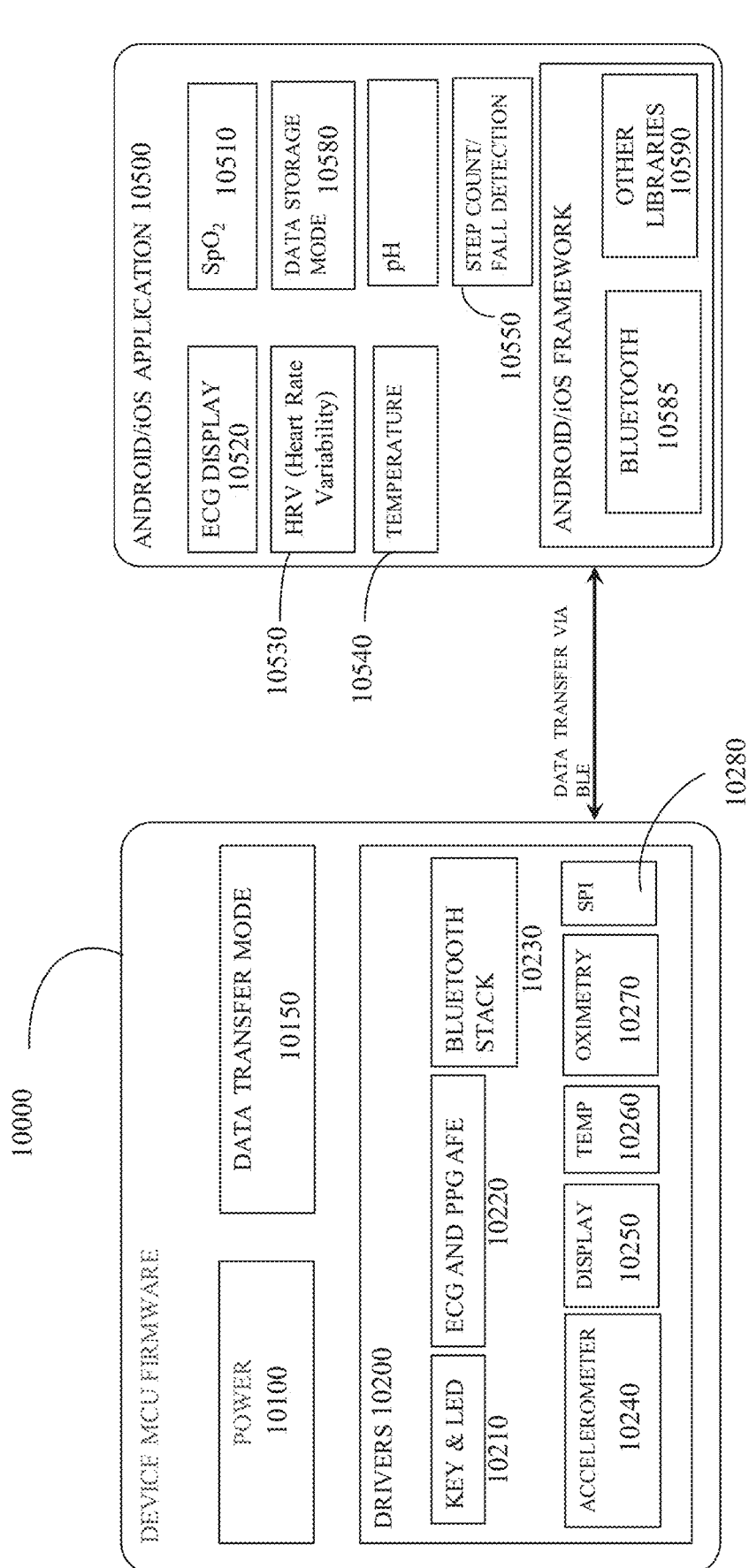

FIG. 10 is an example diagram of a software architecture of a vital signs monitoring patch with display in accordance with certain implementations.

Figures 11A, 11B:
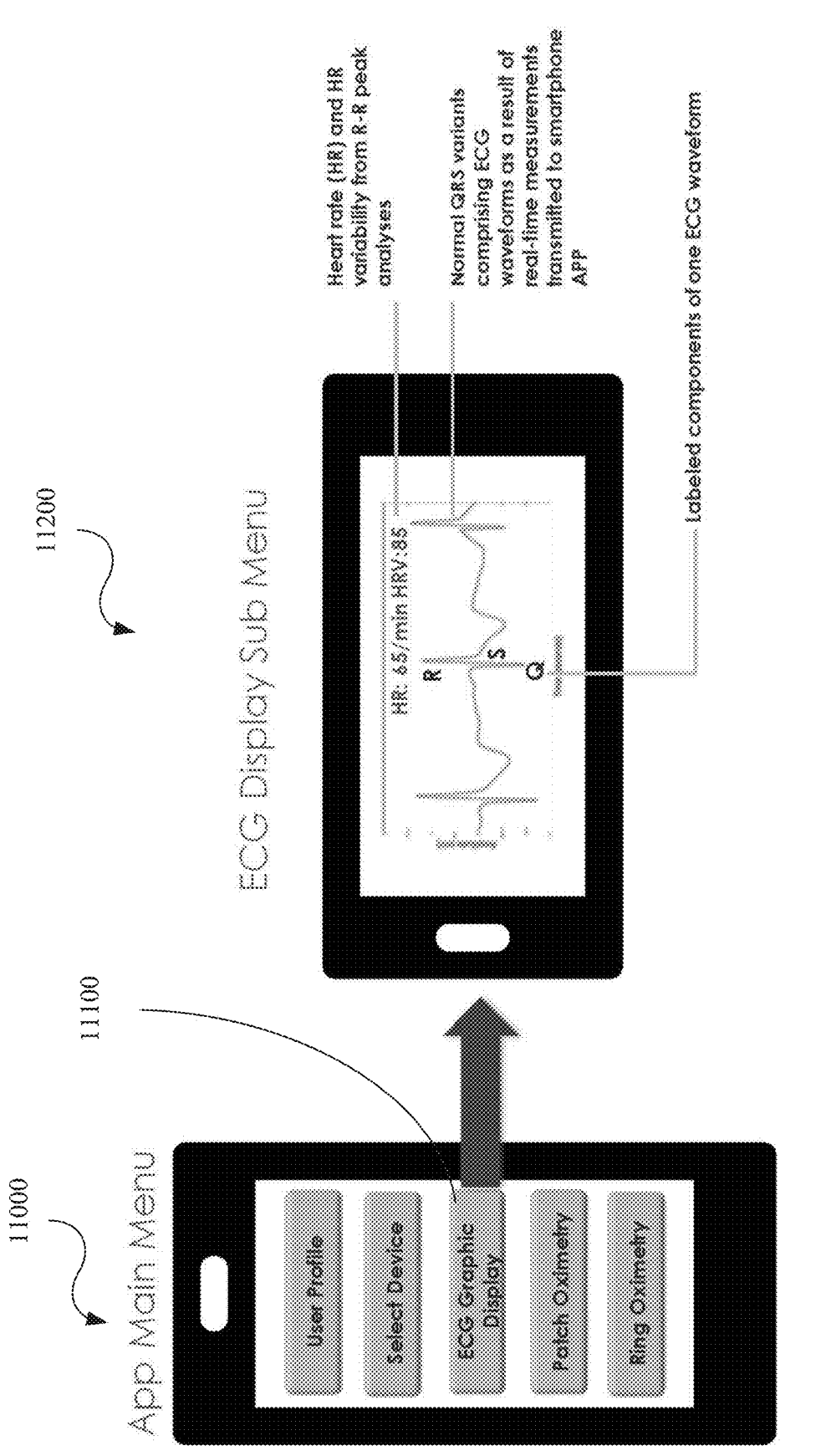

FIGS. 11A-B are an example diagram of an interface screen on a device for interacting with a vital signs monitoring patch with display in accordance with certain implementations.

Figures 12A, 12B:
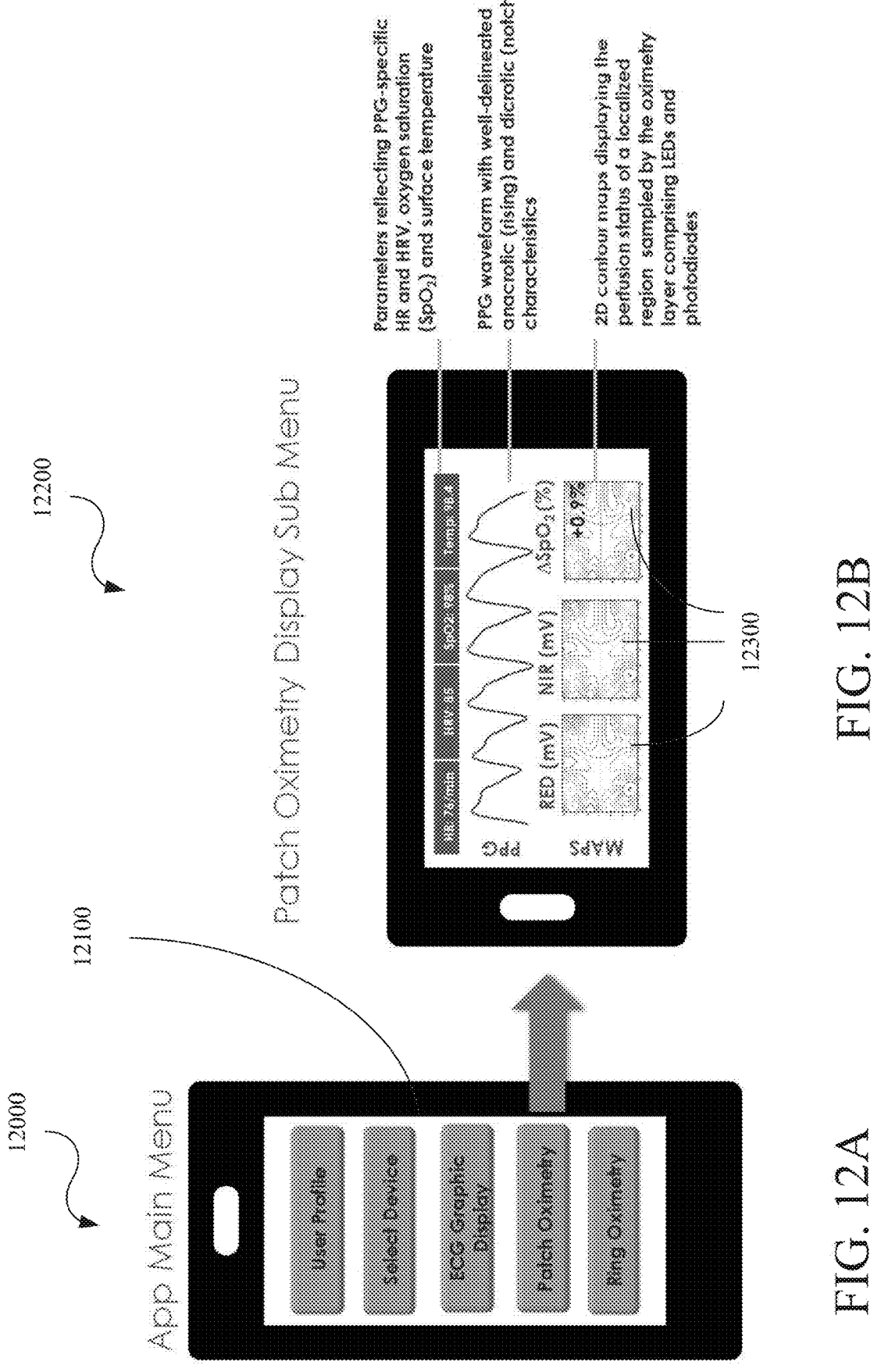

FIGS. 12A-B are an example diagram of an interface screen on a device for interacting with a vital signs monitoring patch with display in accordance with certain implementations.

Figure 13:
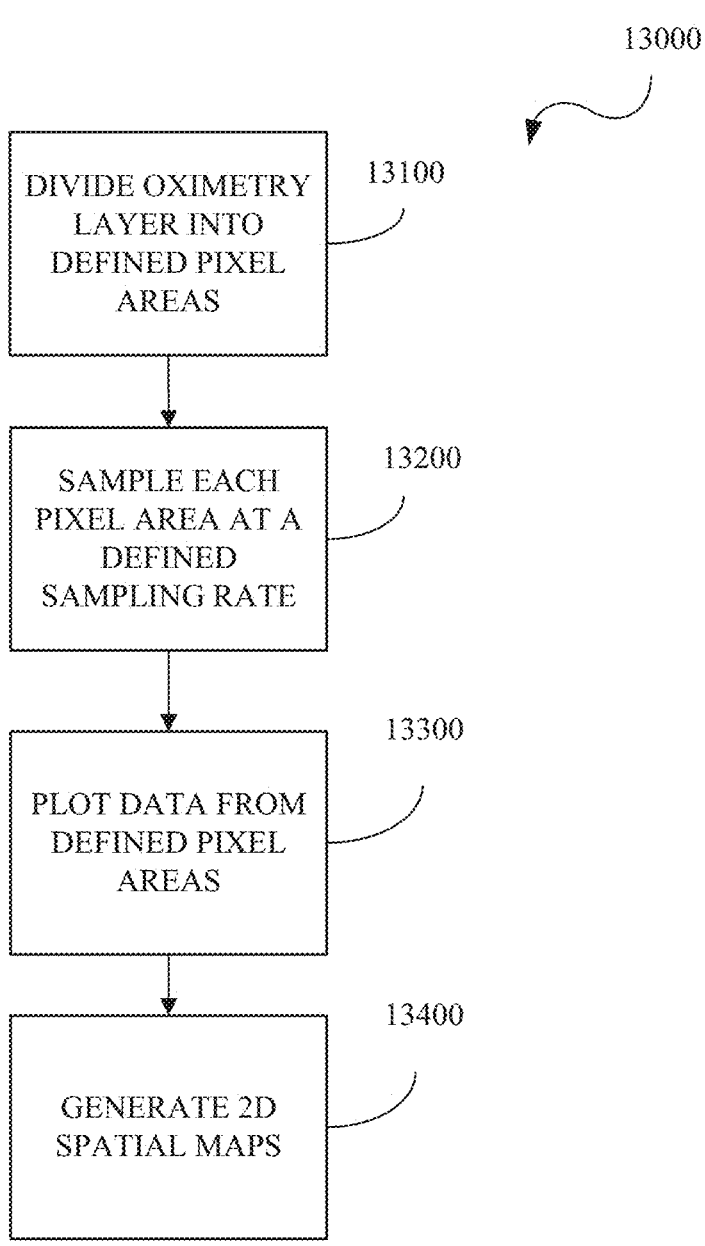

FIG. 13 is a flowchart for reflection mode oximetry measurement for a vital signs monitoring patch with display in accordance with certain implementations.

Figure 14:
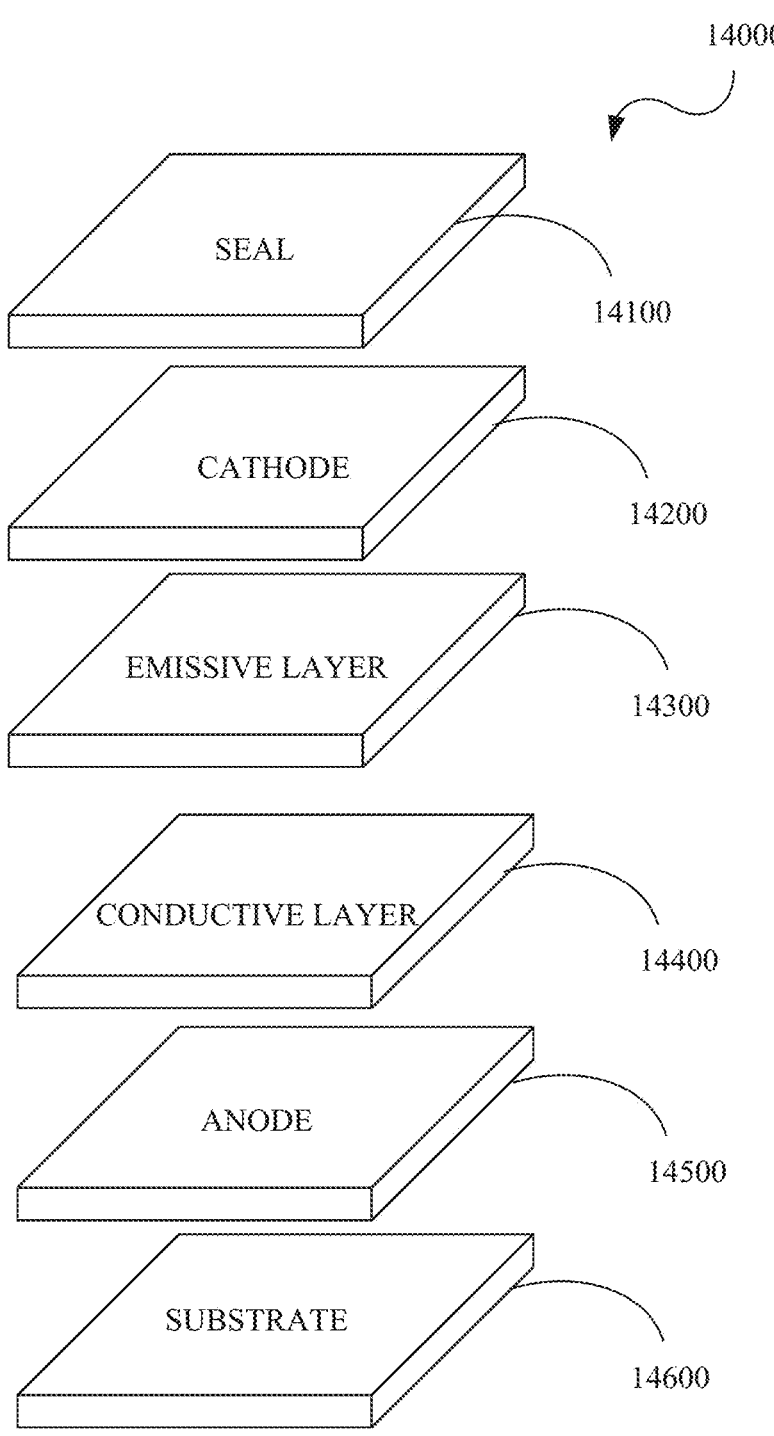

FIG. 14 is a diagram of an example display architecture for a vital signs monitoring patch with display in accordance with certain implementations.

Figure 15:
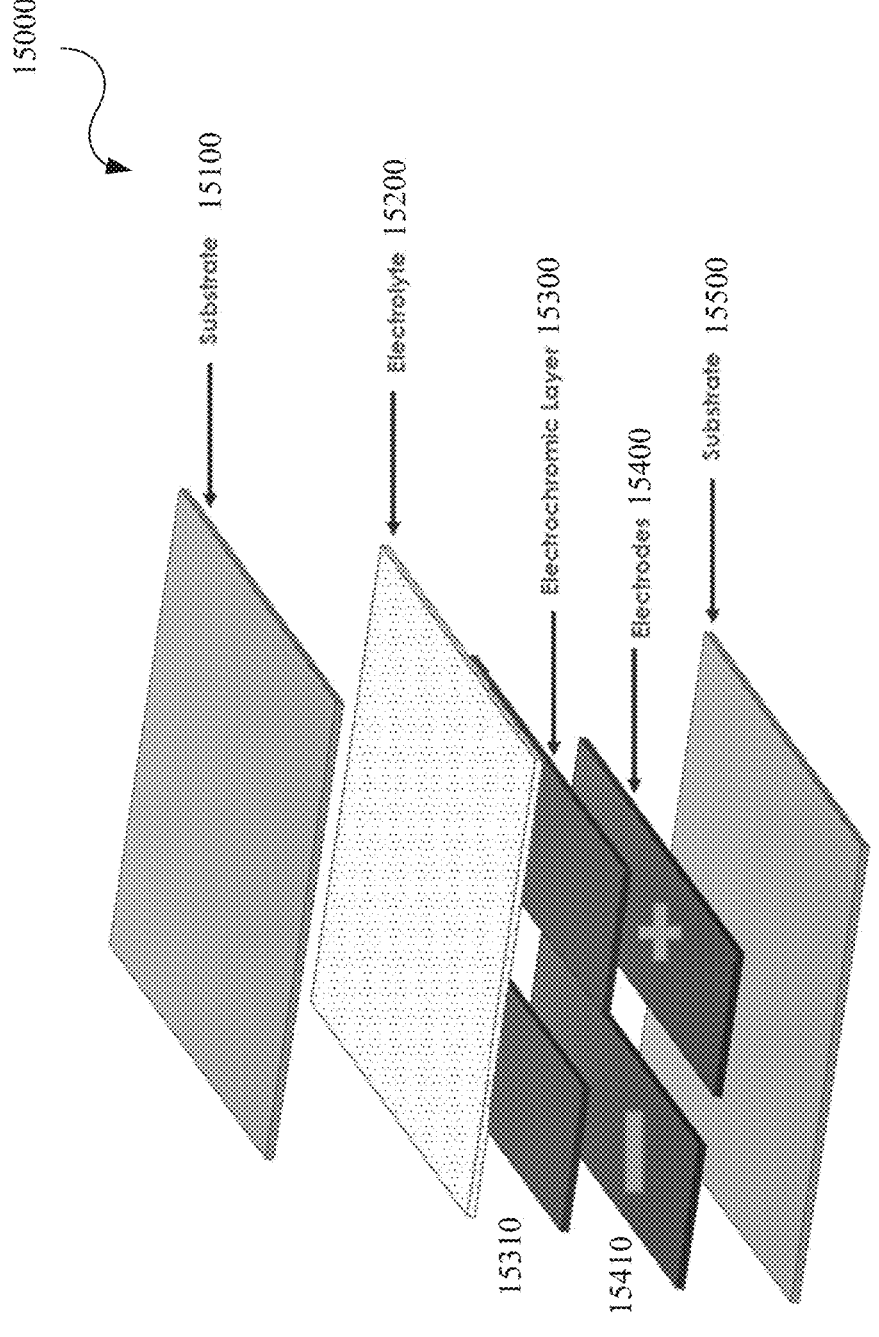

FIG. 15 is a diagram of an example display architecture for a vital signs monitoring patch with display in accordance with certain implementations.

Figure 16A:
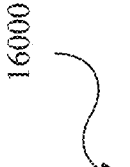
Figure 16A:
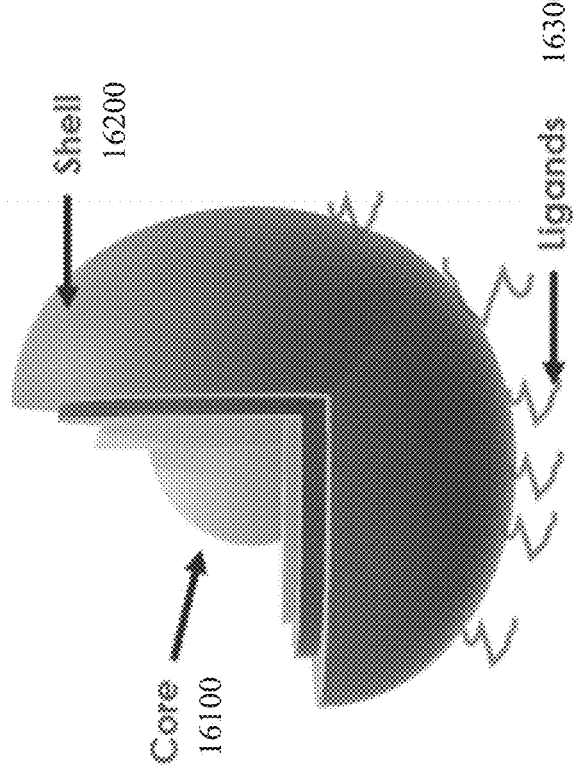

FIGS. 16A and 16 B are diagrams of an example display architecture for a vital signs monitoring patch with display in accordance with certain implementations.

DETAILED DESCRIPTION

The figures and descriptions provided herein may be simplified to illustrate aspects of the described embodiments that are relevant for a clear understanding of the herein disclosed processes, machines, manufactures, and/or compositions of matter, while eliminating for the purpose of clarity other aspects that may be found in typical similar devices, systems, compositions and methods. Those of ordinary skill may thus recognize that other elements and/or steps may be desirable or necessary to implement the devices, systems, compositions and methods described herein. However, because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art in light of the discussion herein.

Embodiments are provided throughout so that this disclosure is sufficiently thorough and fully conveys the scope of the disclosed embodiments to those who are skilled in the art. Numerous specific details are set forth, such as examples of specific aspects, devices, and methods, to provide a thorough understanding of embodiments of the present disclosure. Nevertheless, it will be apparent to those skilled in the art that certain specific disclosed details need not be employed, and that embodiments may be embodied in different forms. As such, the exemplary embodiments set forth should not be construed to limit the scope of the disclosure.

The terminology used herein is for the purpose of describing particular embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, steps, operations, elements, and/or components, but do not preclude the presence or addition of one or more other features, steps, operations, elements, components, and/or groups thereof.

The steps, processes, and operations described herein are thus not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

Yet further, although the terms first, second, third, etc. may be used herein to describe various elements, steps or aspects, these elements, steps or aspects should not be limited by these terms. These terms may be only used to distinguish one element or aspect from another. Thus, terms such as "first," "second," and other numerical terms when used herein do not imply a sequence or order unless clearly indicated by the context. Thus, a first element, step, component, region, layer or section discussed below could be termed a second element, step, component, region, layer or section without departing from the teachings of the disclosure.

As used herein, the terminology "determine" and "identify," or any variations thereof includes selecting, ascertaining, computing, looking up, receiving, determining, establishing, obtaining, or otherwise identifying or determining in any manner whatsoever using one or more of the devices and methods are shown and described herein.

As used herein, the terminology "example," "the embodiment," "implementation," "aspect," "feature," or "element" indicates serving as an example, instance, or illustration. Unless expressly indicated, any example, embodiment, implementation, aspect, feature, or element is independent of each other example, embodiment, implementation, aspect, feature, or element and may be used in combination with any other example, embodiment, implementation, aspect, feature, or element.

As used herein, the terminology "or" is intended to mean an inclusive "or" rather than an exclusive "or." That is unless specified otherwise, or clear from context, "X includes A or B" is intended to indicate any of the natural inclusive permutations. That is if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from the context to be directed to a singular form.

As used herein, the terminology "computer" or "computing device" includes any unit, or combination of units, capable of performing any method, or any portion or portions thereof, disclosed herein. For example, the "computer" or "computing device" may include at least one or more processor(s).

As used herein, the terminology "processor" indicates one or more processors, such as one or more special purpose processors, one or more digital signal processors, one or more microprocessors, one or more controllers, one or more microcontrollers, one or more application processors, one or more central processing units (CPU)s, one or more graphics processing units (GPU)s, one or more digital signal processors (DSP)s, one or more application specific integrated circuits (ASIC)s, one or more application specific standard products, one or more field programmable gate arrays, any other type or combination of integrated circuits, one or more state machines, or any combination thereof.

As used herein, the terminology "memory" indicates any computer-usable or computer-readable medium or device that can tangibly contain, store, communicate, or transport any signal or information that may be used by or in connection with any processor. For example, a memory may be one or more read-only memories (ROM), one or more random access memories (RAM), one or more registers, low power double data rate (LPDDR) memories, one or more cache memories, one or more semiconductor memory devices, one or more magnetic media, one or more optical media, one or more magneto-optical media, or any combination thereof.

As used herein, the terminology "instructions" may include directions or expressions for performing any method, or any portion or portions thereof, disclosed herein, and may be realized in hardware, software, or any combination thereof. For example, instructions may be implemented as information, such as a computer program, stored in memory that may be executed by a processor to perform any of the respective methods, algorithms, aspects, or combinations thereof, as described herein. Instructions, or a portion thereof, may be implemented as a special purpose processor, or circuitry, that may include specialized hardware for carrying out any of the methods, algorithms, aspects, or combinations thereof, as described herein. In some implementations, portions of the instructions may be distributed across multiple processors on a single device, on multiple devices, which may communicate directly or across a network such as a local area network, a wide area network, the Internet, or a combination thereof.

As used herein, the term "application" refers generally to a unit of executable software that implements or performs one or more functions, tasks or activities. For example, applications may perform one or more functions including, but not limited to, vital signs monitoring, health monitoring, telephony, web browsers, e-commerce transactions, media players, travel scheduling and management, smart home management, entertainment, and the like. The unit of executable software generally runs in a predetermined environment and/or a processor.

The non-limiting embodiments described herein are with respect to patches or devices and methods for making the patches or devices, where the patches or devices are vital signs monitoring or health signs monitoring patches or devices with integrated display. The patch or device and method for making the patch or device with integrated display may be modified for a variety of applications and uses while remaining within the spirit and scope of the claims. The embodiments and variations described herein, and/or shown in the drawings, are presented by way of example only and are not limiting as to the scope and spirit. The descriptions herein may be applicable to all embodiments of the device and the methods for making the devices.

Disclosed herein are implementations of health or vital (collectively "vital") signs monitoring patches or devices with integrated display (collectively "patches") and methods for making the patches. The vital signs monitoring patch with display is an external on-body, skin-contact patch. The patch is easily attached and removed from the user. The patch may use a combination of sensors, printed electronics, adhesives, batteries, display electronics, flexible materials or enclosures. In an implementation, the vital signs monitoring patch with display includes flexible display layers based on organic, electrochromic, or quantum dot display techniques and materials. The parameters that may be displayed on the patch include, but are not limited to, heart rate (HR), heart rate variability (HRV), oxygen saturation ($SpO_2$), body surface temperature, pH levels and the like The vital signs monitoring patch with display integrates multiple sensing modalities such as, but not limited to, single or multi-lead electrocardiogram (ECG), photoplethysmography (PPG), oxygen saturation mapping (oximetry), temperature monitoring and pH monitoring in one wearable and disposable device for detecting pulsatile signals or the lack thereof. The device and captured data is used to monitor injuries over time such as open and/or closed wounds, trauma, pressure sores, post-surgical skin grafts, hydration, thermoregulation, hyperhidrosis, infection, muscle fatigue, dialysis, firefighting, stress, ischemic tissue status, and the like, by tracking the data from the multiple sensing modalities over time and the patch coverage area.

In an implementation, the vital signs monitoring patch with display is disposable. The disposability aspect means that internal electronics and power supply are sealed from external exposure. This disposability aspect of the patch permits sealing of the structure to provide a dust tight patch. In addition, the patch provides protection against temporary immersion in water. In an implementation, the patch may have an International Electrotechnical Commission (IEC) protection rating of IPX 67. Due its disposability, the patch may have a small form factor including both size and weight. This makes it easy for the user to wear without much discomfort.

In an implementation, the variety of sensors may include, but is not limited to, a single lead ECG sensor, a PPG sensor, temperature sensors, and an accelerometer. In an implementation, the PPG sensor is a reflection mode oximetry measurement sensor. In an implementation, the reflection mode oximetry measurement sensor may include light emitting diodes (LEDs) and photodiodes. The LEDs may be red LEDs, near infrared (NIR) LEDs, and/or green LEDs.

In an implementation, the patch may include a low power microcontroller with Bluetooth® for communication, an analog front-end (AFE) for measuring ECG and oximetry signals (PPG) and oxygen saturation ($SpO_2$)), screen printed Silver-Silver Chloride electrodes (Ag—AgCl), an accelerometer, temperature sensor, pH sensor, and an oximetry layer including the LEDs and photodiodes on the same layer (or plane).

Power for the patch is internally supplied by a flexible battery as described herein. The flexible battery may permit the patch to be run in a continuous mode of operation for a defined time period. For example, the defined time period may be 7 days. The data from the patch may be communicated to a mobile device for display or analysis. In an implementation, the communication may be done via wireless, Bluetooth®, and the like. The data may include ECG live data, heart rate, heart rate variability, fall detection, $SpO_2$, pH, body surface temperature, and the like. In an implementation, the flexible battery is sealed. In an implementation, the flexible battery is rechargeable.

Figure 1:
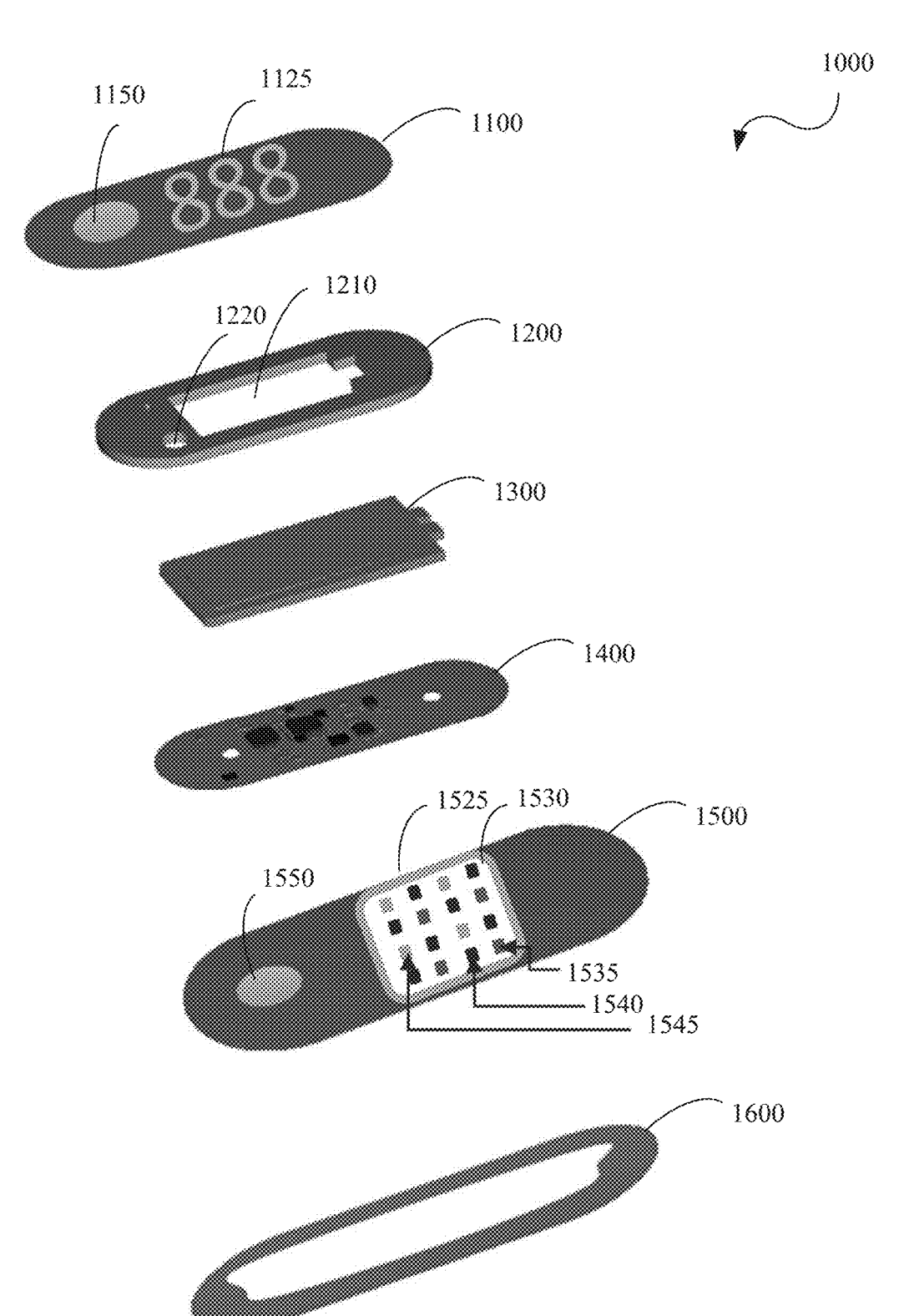
FIG. 1 is a diagram of the multiple layers in a vital signs monitoring patch with display in accordance with certain implementations.
Figures 2A, 2B, 2C, 2D, 2E:
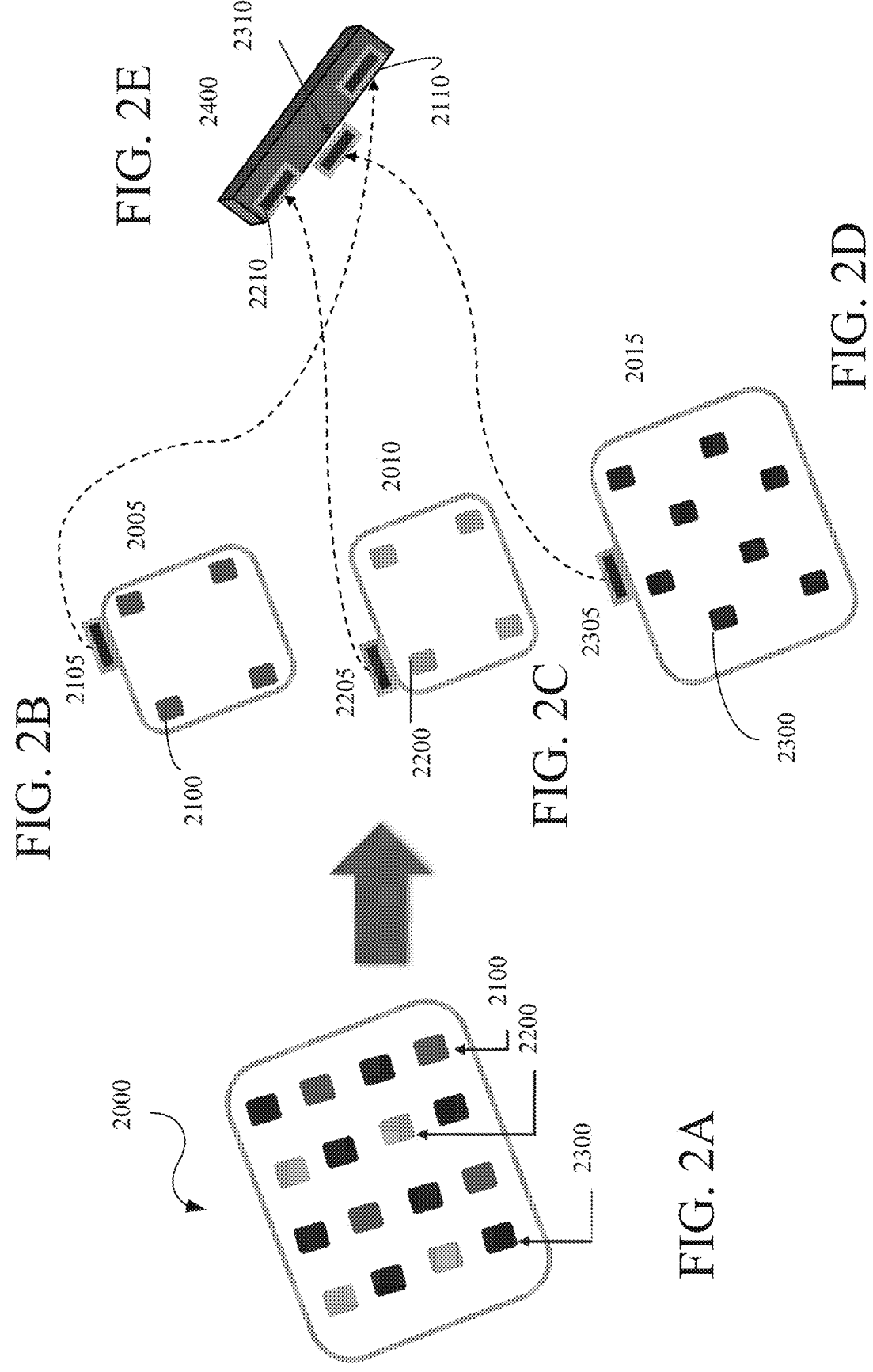
FIGS. 2A-E are diagrams of reflection mode oximetry measurement components in accordance with certain implementations.

FIG. 1 is a diagram of the multiple layers in a vital signs monitoring patch with display 1000 in accordance with certain implementations.

Layer 1 of the vital signs monitoring patch with display 1000 is a user access layer 1100 which includes a display section 1125 and a top ECG electrode 1150. The display section 1100 is a printed light emitting device which displays heart rate information from ECG electrodes, $SpO_2$ levels, body surface temperature, and the like. In an implementation, the display section 1100 is a 3-digit 7-segment display. In an implementation, the display section 1100 may include multiple display sections for displaying different physiological parameters as described herein. In an implementation, the display section 1100 is implemented using organic, electrochromic, or quantum dot display techniques and materials as described herein. In an implementation, the display section 1100 is flexible. The top ECG electrode 1150 is a screen-printed Ag—AgCl ECG electrode which is touchable or engageable by a user to complete an ECG sensor circuit.

Layer 2 is a polyethylene foam layer 1200 which may adhere to the user access layer 1100. The polyethylene foam layer 1200 may have a laser cut-out 1210 for encompassing and protecting a power supply unit 1300 and an assembled printed circuit board (PCBA) layer 1400, and a cut-out 1220 for an on/off plunger.

Layer 3 is a power supply unit 1300. In an implementation, the power supply unit 1300 may be a stack of Lithium polymer or similar batteries providing 3.3 V and 140 mAh, for example. In an implementation, the power supply unit 1300 may be a flexible battery. The power supply unit 1300 provides power to the various components on the vital signs monitoring patch with display 1000.

Layer 4 is the PCBA layer 1400 which may include active and passive components as described herein and adhere to layer 2. In an implementation, the PCBA layer 1400 may include, but is not limited to, an accelerometer, pH sensor, and temperature sensor(s). In an implementation, the accelerometer may be used for activity tracking such as steps, sleep efficiency, and sleep staging. In an implementation, one or more temperature sensors may be used to determine a temperature profile for a wound, for example. The one or more temperature sensors may sense or monitor surface temperatures of a localized body area. In an implementation, the pH sensor may monitor the pH levels of a localized body area. The pH level may vary from 0 to 14 and as stated herein, may be displayed via layer 1. For example, pH of normal healing wounds ranges from 5.5 to 6.5 and pH of nonhealing wounds is greater than 6.5. In an implementation, the pH sensors may be potentiometric pH sensors. In an implementation, the pH sensors may be implemented using carbon/polyaniline and Ag—AgCl electrodes.

A bottom side of a layer 5 is shown in FIG. 1. Layer 5 is a sensor layer 1500 which may adhere to the PCBA layer 1400. The sensor layer 1500 may include reflection mode oximetry measurement components 1525 and a bottom ECG electrode 1550. In an implementation, the bottom ECG electrode 1550 may be a screen-printed Ag—AgCl ECG electrode which interfaces with a user skin via a hydrogel layer. For example, the bottom ECG electrode 1550 may contact the skin area on the chest near the heart. Other skin surface areas may also be used. Operationally, a user may contact the top ECG electrode 1150, for example using an index finger of the hand from the opposing side of the body (right hand if patch is placed near heart). Contact of the index finger with the top ECG electrode 1150 completes the circuit with the bottom ECG electrode 1550 for single lead (two electrode-based) ECG measurements.

In an implementation, the data may be streamed to a device application through a Bluetooth® connection. FIGS. 11A-B are an example diagram of an interface screen 11000 on a device for interacting with a vital signs monitoring patch with display in accordance with certain implementations. The interface screen 11000 may have a link or tab 11100 for selection of a sub-menu for EGG graphic display 11200. The ECG graphic display 11200 may stream the live ECG signal showing distinct QRS complexes and reports the heart rate and heart rate variability derived from the R-R peak intervals.

Oximeters sense oxygen saturation in tissues by optically quantifying concentrations of oxyhemoglobin ($HbO_2$) and deoxyhemoglobin (Hb). Pulse oximetry is one modality for ratiometric optical measurements on pulsatile arterial blood by leveraging photoplethysmography (PPG) at a minimum of two distinct wavelengths. PPG comprises optoelectronic components such as LEDs and photodiodes. In an implementation, the reflection mode oximetry measurement components 1525 (also referred to as an oximetry layer) of layer 5 may include a 4×4 array 1530 of red LEDs (4) 1535, NIR LEDs (4) 1545, and photodiodes (8) 1540 for a total of 16 pixels to facilitate reflection mode oximetry measurements. In an implementation, the 4×4 array 1530 provides a flexible reflection oximetry platform for single point measurements of heart rate, heart rate variability, $SpO_2$ and 2D oxygenation mapping of localized tissues.

Figure 3:
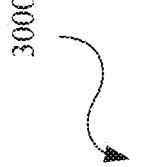
FIG. 3 is a diagram of reflection mode oximetry measurement components in accordance with certain implementations.
Figure 3:
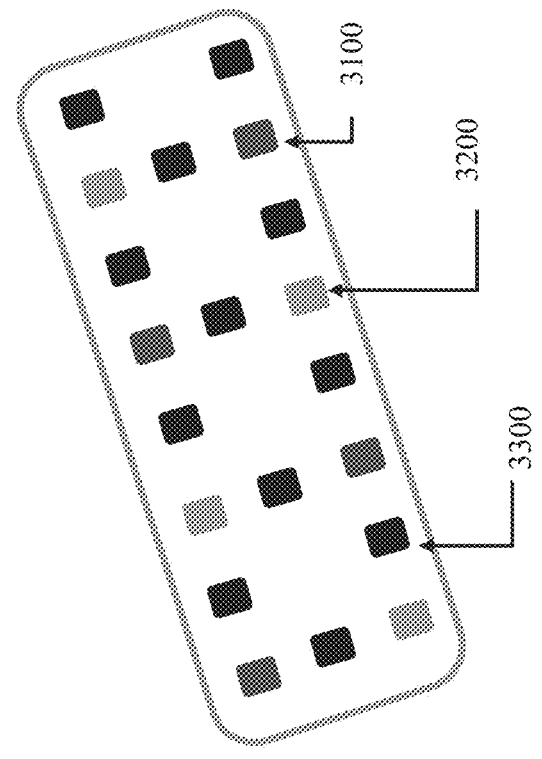

The molar absorption coefficients of $HbO_2$ and Hb are disparate at the red and NIR wavelengths. The red LEDs 1535 and the NIR LEDs 1545 act as emitters (converting electrical energy into light energy) where light is transmitted at 610 nm and 725 nm wavelengths, respectively. In an implementation and as shown in FIG. 3, red and green (530 nm) may also be used as LED combinations.

The photodiodes 1540 sense the non-absorbed light from the LEDs. The signals are inverted by means of an operational amplifier. These signals are interpreted as light that has been absorbed by the tissue being probed and are assigned to direct current (DC) and alternating current (AC) components. The DC component is treated as light absorbed by the tissue, venous blood, and non-pulsatile arterial blood. The AC component is treated as pulsatile arterial blood.

Data from the reflection mode oximetry measurement components 1525 of layer 5 may be streamed to a device application. FIGS. 12A-B are an example diagram of an interface screen 12000 on a device for interacting with a vital signs monitoring patch with display in accordance with certain implementations. The interface screen 12000 may have a link or tab 12100 for selection of a sub-menu for Patch Oximetry display 12200. At the Patch Oximetry display 12200, a user may view a live stream of the PPG waveform with well-delineated anacrotic (rising) and dicrotic (notch) characteristics. In an implementation, the Patch Oximetry display 12200 may display 2D contour maps 12300 in real-time that provide the perfusion status of a localized region sampled by the oximetry layer, where the oximetry layer includes the LEDs and photodiodes. The 2D contour maps 12300 are enabled via the array 1530 as described with respect to FIGS. 2A-E, and the PCBA layer 7600 of FIG. 7, for example. In an implementation, the Patch Oximetry display 12200 may display parameters reflecting PPG-specific heart rate, heart rate variability, and oxygen saturation. In an implementation, the Patch Oximetry display 12200 may display surface temperature, pH levels, and other biomarker or physiological parameters.

In an implementation, the size of the array may vary without departing from the scope of the specification or claims. In an implementation, the number of pixels may vary without departing from the scope of the specification or claims. In an implementation, the number of LEDs for specific wavelengths or frequencies may vary without departing from the scope of the specification or claims. In an implementation, different wavelengths or frequencies may be used without departing from the scope of the specification or claims.

Layer 6 is a spacer ribbon-like layer 1600 around layer 5. The spacer ribbon-like layer 1600 may bond to the skin of the user and may hold the entire patch in position on the skin. For example, the spacer ribbon-like layer 1600 may be a medical tape which consists of a porous, highly breathable, white elastic multilayer polyurethane/synthetic rubber based non-woven fabric. The non-woven fabric may be coated on one side with a pressure sensitive adhesive which bonds to a user skin surface and an adhesive on the other side for bonding with layer 5.

As referenced herein above, the vital signs monitoring patch with display may also include an application which may run on a device such as mobile devices, end user devices, cellular telephones, Internet Protocol (IP) devices, mobile computers, laptops, handheld computers, PDAs, personal media devices, smartphones, notebooks, notepads, phablets, smart watches, and the like (collectively "user device"). The vital signs monitoring patch with display may wirelessly communicate with the user device and the application together with the user device may analyze, display and provide alerts to a user the vitals signs data collected by the vital signs monitoring patch with display. The vital signs monitoring patch with display may interface with the application to measure, stream and record real-time data for providing comprehensive sensing information to user(s). FIGS. 11A-B and FIGS. 12A-B are example diagrams of interface screens for reviewing the sensor data as described herein.

FIGS. 2A-E are diagrams of reflection mode oximetry measurement components 2000 in accordance with certain implementations. The reflection mode oximetry measurement components 2000 may include an array of red LEDs 2100, NIR LEDs 2200, and photodiodes 2300, where a shaded area reflects a light emitting area. In an implementation, the reflection mode oximetry measurement components 2000 may include a red LED array layer 2005, a NIR LED array layer 2010, and a photodiode array layer 2015. The red LED array layer 2005 may include the red LEDs 2100 in a defined pattern and a connector 2105. The NIR LED array layer 2010 may include the NIR LEDs 2200 in a defined pattern and a connector 2205. The photodiode array layer 2015 may include the photodiodes 2300 in a defined pattern and a connector 2305. The reflection mode oximetry measurement components 2000 may include an interface board 2400 which connects to a PCBA such as PCBA layer 1400 of FIG. 1. The connectors 2105, 2205, and 2305 each connect to connectors 2110, 2210, and 2310, respectively, on the interface board 2400 to carry or send signals to the appropriate components on the PCBA.

In an implementation, the red LEDs 2100 may emit approximately at 610 nm and the NIR LEDs 2200 may emit around 725 nm. In an implementation, the LED active areas for the red LEDs 2100 and the NIR LEDs 2200 may be approximately 7.0×7.0 mm². In an implementation, the photodiode active area may be approximately 7.0×7.0 mm². In an implementation, the spacing between the red LEDs 2100, NIR LEDs 2200, and photodiodes 2300 may be approximately 5.0 mm AC and DC signal magnitudes drop off exponentially with increased spacing between emitters and detectors (or photodiodes). The array configuration and spacing of the red LEDs 2100, NIR LEDs 2200, and photodiodes 2300 enable 2D contour mapping for the skin surface proximate to the patch contact area. This permits determination of blood flow, temperature, and other physiological parameters at different points relative to the patch contact area and therefore the physiological conditions at different points with respect to, for example, a wound. For example, analysis of the 2D contour maps may show healing at one part of the wound but not at another part of the wound.

FIG. 3 is a diagram of reflection mode oximetry measurement components 3000 in accordance with certain implementations. In an implementation, the reflection mode oximetry measurement components 3000 may include an array of red LEDs 3100, green LEDs 3200, and photodiodes 3300. In an implementation, the red LEDs 3100 may emit approximately at 610 nm and the green LEDs 3200 may emit around 530 nm. In an implementation, the LED active areas for the red LEDs 3100 and the green LEDs 3200 may be approximately 10.0×10.0 mm². In an implementation, the spacing between the red LEDs 3100, NIR LEDs 3200, and photodiodes 3300 may be approximately 5.0 mm.

Figure 4:
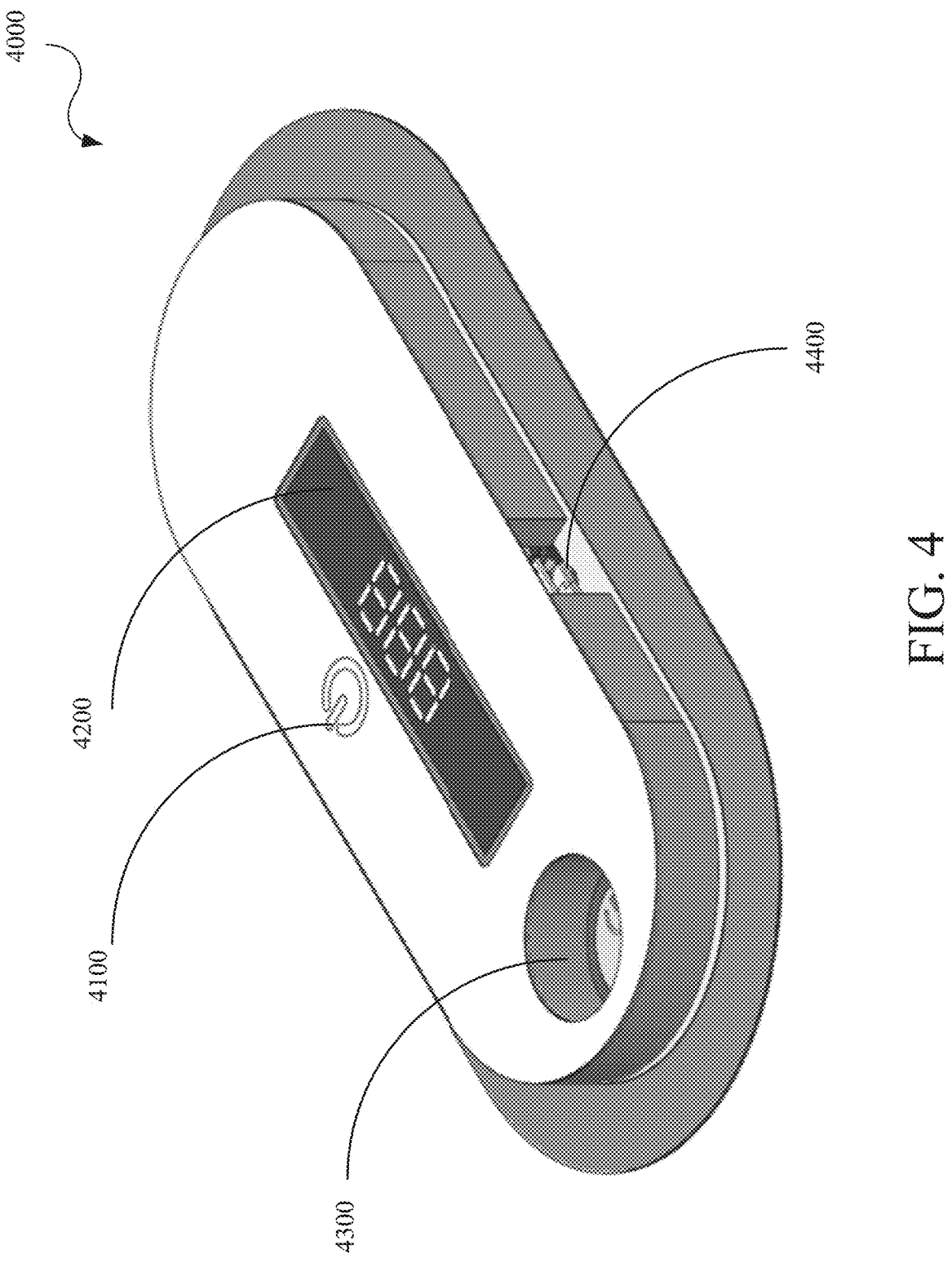
FIG. 4 is a perspective view of a vital signs monitoring patch with display in accordance with certain implementations.
Figure 5:
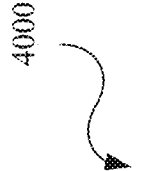
FIG. 5 is a top view of the vital signs monitoring patch with display of FIG. 4 in accordance with certain implementations.
Figure 5:
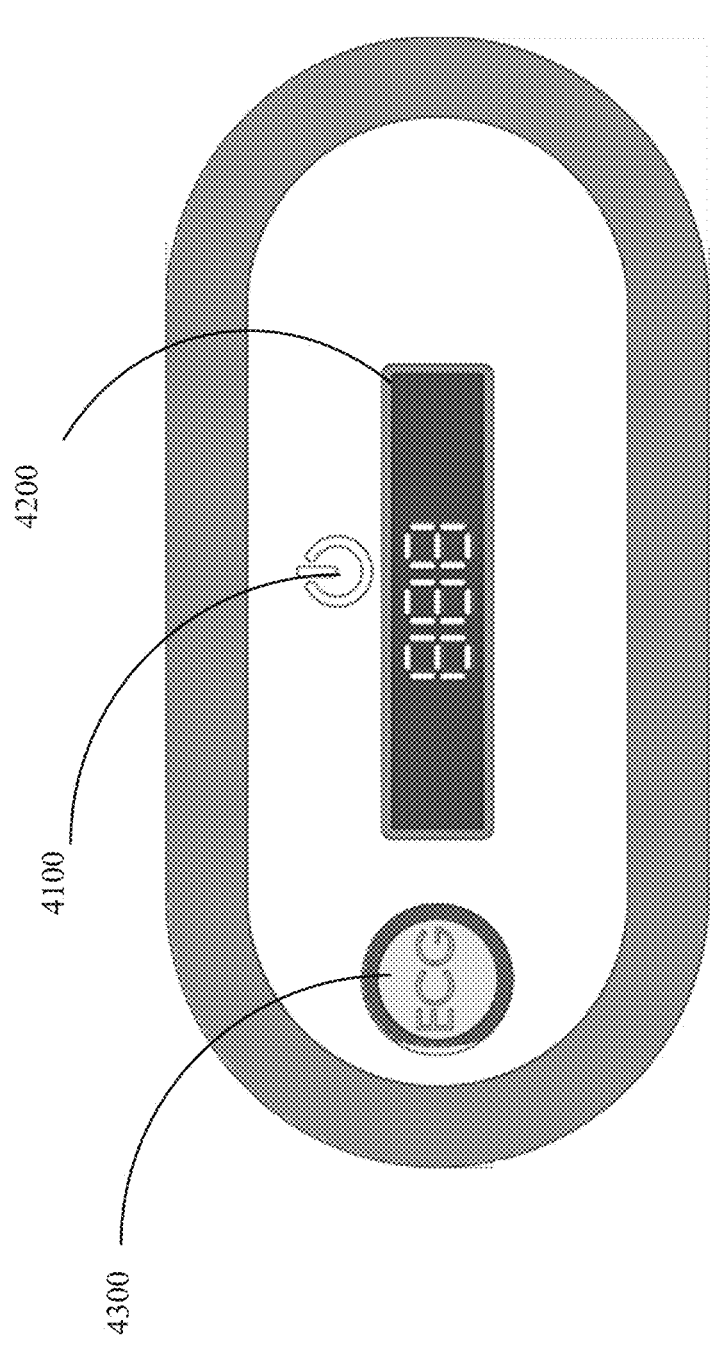
Figure 6:
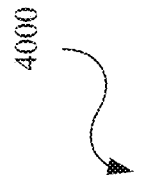
FIG. 6 is a side view of the vital signs monitoring patch with display of FIG. 4 in accordance with certain implementations.
Figure 6:
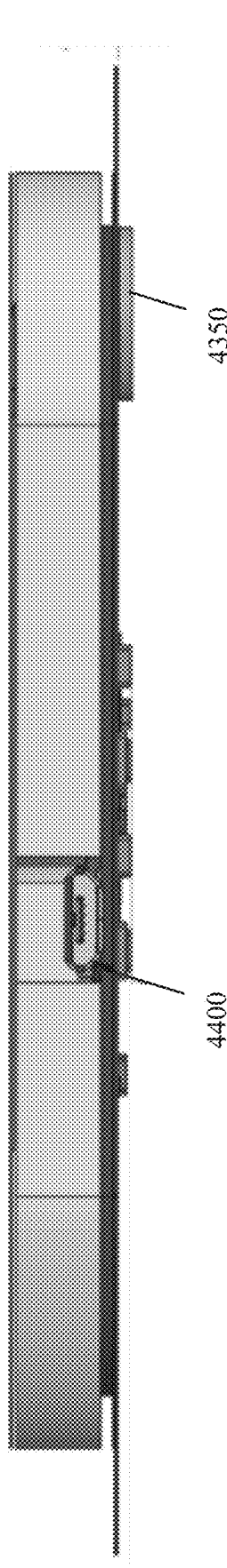

FIG. 4 is a perspective view of a vital signs monitoring patch with display 4000 in accordance with certain implementations. FIG. 5 is a top view of the vital signs monitoring patch with display of FIG. 4 in accordance with certain implementations. FIG. 6 is a side view of the vital signs monitoring patch with display of FIG. 4 in accordance with certain implementations. The vital signs monitoring patch with display 4000 may include a power button 4100, a display section 4200, and a front or top ECG electrode 4300. In an implementation, the vital signs monitoring patch with display 4000 may include a charging port 4400. The power button 4100 is configured to power on or off the vital signs monitoring patch with display 4000. The display section 4200 depicts information related to physiological parameters sensed or captured by the vital signs monitoring patch with display 4000 as described herein. The display section 4200 is implemented as described herein. The front or top ECG electrode 4300 is part of a two ECG electrode configuration, where a bottom of the vital signs monitoring patch with display 4000 includes a bottom ECG electrode 4350 as shown in FIG. 6, and functions or operates as described herein. The front or top ECG electrode 4300 is configured such that accidental or incidental touching of the front or top ECG electrode 4300 is minimized. In an implementation, the front or top ECG electrode 4300 is touchable at a plane below the plane of the display section 4200. The charging port 4400 permits charging of the vital signs monitoring patch with display 4000. In an implementation, the vital signs monitoring patch with display 4000 may include a wireless charger.

Figure 7:
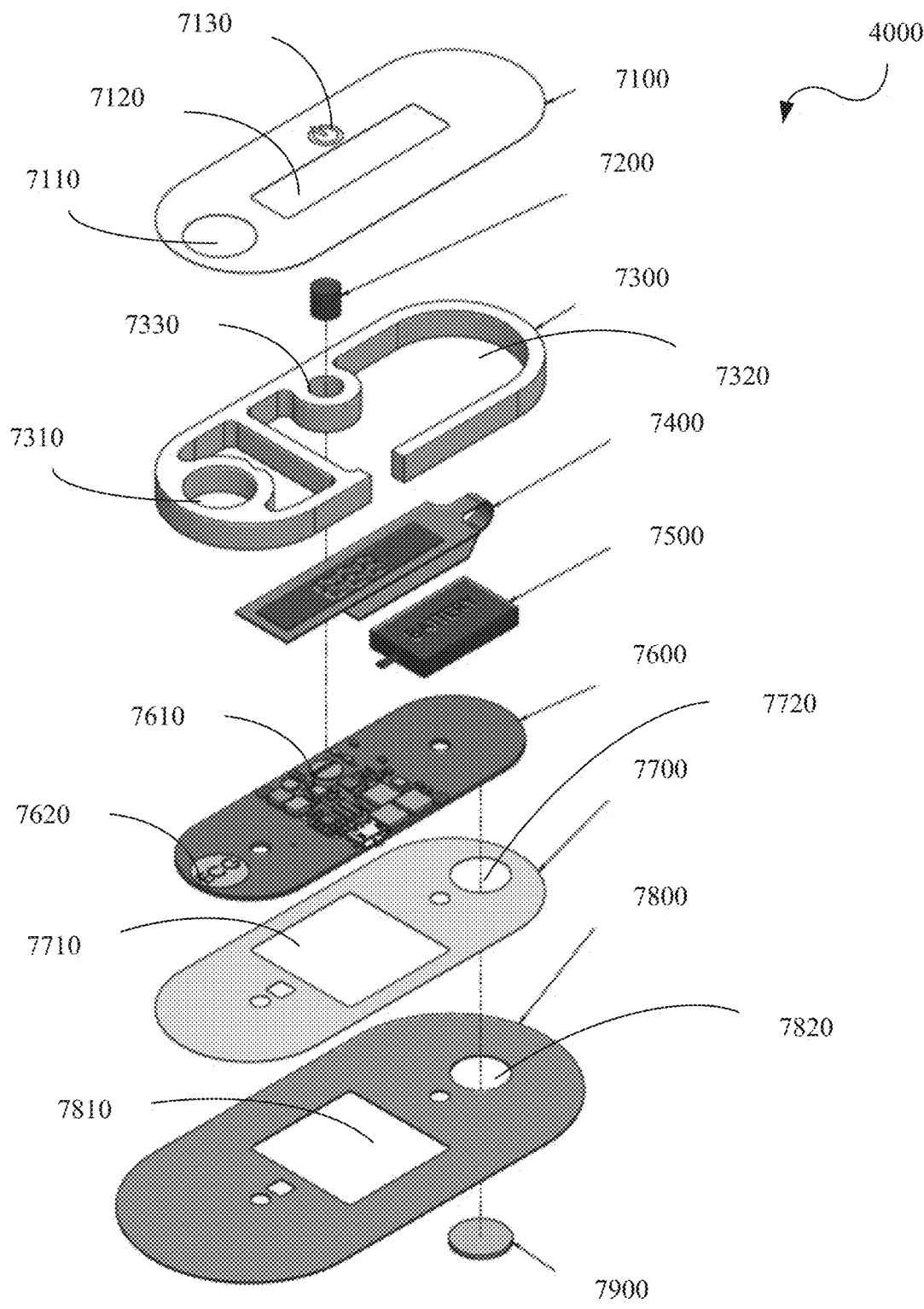
FIG. 7 is a diagram of the multiple layers of the vital signs monitoring patch with display of FIG. 4 in accordance with certain implementations.

FIG. 7 is a diagram of the multiple layers of the vital signs monitoring patch with display 4000 in accordance with certain implementations.

Layer 1 is a top cover 7100 which includes a cut-out 7110 for contact access to a front or top ECG electrode 7620, a cut-out 7120 for a display 7400, and a power button indicator 7130 for a plunger or power button 7200. In an implementation, the top cover 7100 may be sticker paper or acrylic material which includes an adhesive on the bottom surface of the top cover 7100.

Layer 2 is the plunger or power button 7200 which is in contact with the top cover 7100 at the power button indicator 7130 and with the PCBA layer 7600 of layer 6 via a cut-out 7330 in layer 3. Pressing at the power button indicator 7130 engages the plunger or power button 7200, which in turn switches a switch on the PCBA layer 7600, for example, to power on the vital signs monitoring patch with display 4000.

Layer 3 is a foam spacer 7300 which includes a cut-out 7310 for the front or top ECG electrode 7620, a cut-out 7320 for the display 7400, and a cut-out 7330 for the plunger or power button 7200. In an implementation, the foam spacer 7300 is a double sided, adhesive coated urethane foam tape for bonding with the top cover 7000 and the PCBA layer 7600. In an implementation, the foam spacer 7300 has a defined thickness to mitigate inadvertent ECG circuit completion, provide placement of the display 7400, and provide placement of a battery 7500.

Layer 4 is the display 7400. In an implementation, the display 7400 is a 3-digit, 7-segment display which depicts at least the physiological parameters described herein. In an implementation, the display 7400 is implemented as described herein. The display 7400 is electrically and mechanically connected to the PCBA layer 7600.

Layer 5 is the battery 7500. In an implementation, the battery 7500 is a polymer Lithium battery or battery stack. In an implementation, the battery 7500 is rechargeable. The battery 7500 is connected to the PCBA layer 7600 and/or the display 7400.

Layer 6 is the PCBA layer 7600. The PCBA 7600 includes active and passive components section 7610, the front or top ECG electrode 7620 on one side or a top surface of the PCBA layer 7600 and a bottom ECG electrode on another side or bottom surface of the PCBA layer 7600.

Layer 7 is a double-sided medical tape layer 7700 which includes a cut-out 7710 for the active and passive components section 7610 and a cut-out 7720 for the bottom ECG electrode. The double-sided medical tape layer 7700 has adhesive on both sides which bonds to the PCBA layer 7600 and the medical tape layer 7800

Layer 8 is the medical tape layer 7800 which includes a cut-out 7810 for the active and passive components section 7610 and a cut-out 7820 for the bottom ECG electrode. The medical tape layer 7800 includes a medical adhesive to bond to the user skin surface.

Layer 9 is a hydrogel conductive adhesive patch 7900 which is connected to the bottom ECG electrode 7630.

FIG. 8 is a bottom view of the PCBA layer 7600 in accordance with certain implementations. A bottom surface 8000 of the PCBA layer 7600, for example, includes a first temperature sensor 8100, a second temperature sensor 8200, a bottom ECG electrode 8300, and reflection mode oximetry measurement components 8400. In an implementation, the bottom ECG electrode 8300 may be a screen-printed Ag—AgCl electrode. In an implementation, the reflection mode oximetry measurement components 8400 may be configured and function and operate as shown in FIGS. 2A-2E. In an implementation, the reflection mode oximetry measurement components 8400 may be configured and function and operate as described in the specification herein. In an implementation, the reflection mode oximetry measurement components 8400 may include red LEDs 8410, NIR LEDs 8420, and photodiodes 8430 which function and operate as described in the specification herein. The first temperature sensor 8100 and the second temperature sensor 8200 permit generation of a temperature profile for a wound, for example, to see whether healing is progressing. The parameters may be displayed on the display 7400 or transmitted to another device which may show, for example, a 2D thermal contour.

FIG. 8A is a diagram of the reflection mode oximetry measurement components 8400 in accordance with certain implementations. The reflection mode oximetry measurement components 8400 may be configured in an array 8405 which may include an array of red LEDs 8410 (shown as R1-R4), array of NIR LEDs 8420 (shown as N1-N4), and an array of photodiodes 8430 (shown as P1-P8), where each array is configured in a defined pattern. Readout from the array 8405 may be implemented by sampling in a raster format. In an implementation, a raster pattern 8500 may be done from top to bottom. In an implementation, the array 8405 may be read out by sampling readout blocks 8600 from readout block 1 to readout block 9 (RB1-RB9). As an illustrative example, RB1 may include P1, R1, N1 and P2, RB2 may include R1, P3, P2 and N2, RB3 may include P3, R2, N2 and P4, RB4 may include N1, P8, P2 and R4, RB5 may include P2, R4, N2 and P6, RB6 may include N2, P6, P4 and R3, RB7 may include P8, N4, R4 and P7, RB8 may include R4, P7, P6 and N3, and RB9 may include P6, N3, R3 and P5.

FIG. 8B is a block diagram of a readout circuit 8600 for a reflection mode oximetry measurement system in accordance with certain implementations. The readout circuit 8600 includes a multiplexor 8700 which is connected to analog front-end (AFE) 8750 and a low power processor with Bluetooth 8800. The AFE 8750 is connected to and receives inputs (IN1-IN3) from photodiodes (PD) 8900 and controls transmission (TX1-TX4) by red LEDs 8910 and NIR LEDs 8920. In an implementation, the red LEDs 8910 and NIR LEDs 8920 are switched on/off by the multiplexer 8700 and a current source within the AFE 8750. The current produced by the photodiodes 8900 are converted into voltages (transimpedance amplifier), time demultiplexed, and digitized back through the AFE 8750 and then transmitted to an application on a mobile device 8950. The AFE 8750, the red LEDs 8910, the NIR LEDs 8920, the photodiodes 8900, and the low power processor with Bluetooth 8800 may function and operate as described in the specification herein.

FIG. 9 is an example diagram of a hardware architecture of a vital signs monitoring patch with display 9000 in accordance with certain implementations. The vital signs monitoring patch with display 9000 includes printed Ag—AgCl electrodes 9100, negative and a positive electrodes, for taking ECG measurements. In an implementation, the printed Ag—AgCl electrodes 9100 are screen-printed on different sides of a PCB. The Ag—AgCl electrodes 9100 are connected to an analog front-end (AFE) 9200, which further includes connections from an accelerometer 9300 and a PPG sensor 9400 (shown as oximetry SpO₂) The AFE 9200 is connected to a processor 9500, which is further connected to a LED display 9600, temperature sensor(s) 9700, pH sensor 9800, and antenna 9900. In an implementation, the processor 9500 is a low power MCU with integrated Bluetooth®. In an implementation, the antenna 9900 is a Bluetooth® which may communicate with a device 9950 using a corresponding antenna 9975. In an implementation, the hardware architecture may, in part, be implemented on the PCBA layer 7600.

FIG. 10 is an example diagram of a software architecture of a vital signs monitoring patch with display 10000 in accordance with certain implementations. A processor software/firmware of the vital signs monitoring patch with display 10000 includes, but is not limited to, a power module 10100, a data transfer module 10150, and drivers 10200 for the LEDs 10210, AFE 10220, Bluetooth® stack 10230, accelerometer 10240, display 10250, temperature sensor 10260, oximetry 10270, serial peripheral interface 10280, ECG sensor, and the like. An application device 10500 may include, but is not limited to, applications to process and display PPG data 10510, ECG data 10520, heart rate variability data 10530, temperature 10540, step count/fall detection (via accelerometer) 10550, blood pressure and like data. The application device further includes a data storage mode 10580, a Bluetooth® stack 10585, and other libraries 10590.

In an implementation, the software/firmware architecture may, in part, be implemented on or with the processor 9500.

FIG. 13 is a flowchart for a method 13000 for reflection mode oximetry measurement for a vital signs monitoring patch with display in accordance with some implementations. The method 13000 includes: dividing 13100 an oximetry layer into a defined set of pixel areas; sampling 13200 each pixel area at a defined sampling rate; plotting 13300 data from the defined set of pixel areas; and generating 13400 2D spatial maps. The method 13000 may be implemented, in part, by the processor 9500, display 9600, and other applicable components.

The method 13000 includes dividing 13100 an oximetry layer into a defined set of pixel areas. Each pixel area of the defined set of pixel areas may include a pair of LEDs and a pair of photodiodes. In an implementation, the pair of LEDs includes a red LED and a NIR LED. In an implementation, the pair of LEDs includes a red LED and a green LED.

The method 13000 includes sampling 13200 each pixel area at a defined sampling rate. Each of the defined set of pixels areas are sampled at a defined sampling rate in a defined pattern. In an implementation, the defined pattern is a raster pattern. In an implementation, the defined sampling rate is 500 Hz.

The method 13000 includes plotting 13300 data from the defined set of pixel areas. The data from the defined set of pixels areas is plotted using one or more interpolation techniques. In an implementation, the one or more interpolation techniques is a nearest neighbor interpolation.

The method 13000 includes generating 13400 2D spatial maps. 2D contour maps are generated from the plotted data for different parameters. For example, a 2D contour map may be generated for the red LEDs, the NIR LEDs, the green LEDs, $\Delta SpO_2$ and other like parameters.

FIG. 14 is a diagram of an example Organic Light Emitting Diode (OLED) stack 14000 for a vital signs monitoring patch with display in accordance with certain implementations. The OLED stack 14000 may include a seal layer 14100, a cathode layer 14200, an emissive layer 14300, a conductive layer 14400, an anode layer 14500, and a substrate 14600. In an implementation, the emissive layer 14300 may be a film of organic compound which emits light in response to current injection. The organic compound may be organic polymers, inks, light emitting polymers, and the like. In an implementation, the conductive layer 14400 may be organic polymers, inks, and the like.

FIG. 15 is a diagram of an example Electrochromic Device (ECD) stack 15000 for a vital signs monitoring patch with display in accordance with certain implementations. The ECD stack may include a substrate 15100, an electrolyte layer 15200, electrochromic layers 15300 and 15310, electrodes 15400 and 15410, and a substrate 15500. In this instance, the electrochromic materials are organic or inorganic substances that change color when charged with electricity. The ECD controls optical properties, such as transmission, absorption, reflectance and/or emittance, in a continual but reversible manner by applying voltage. The ECDs may be printed on plastics, paper, and the like and provide flexible yet robust structures. The ECDs use ultra-low power and are activated by small currents. The ECDs can be integrated with sensors for motion, touch, proximity, temperature and the like.

Figure 16B:
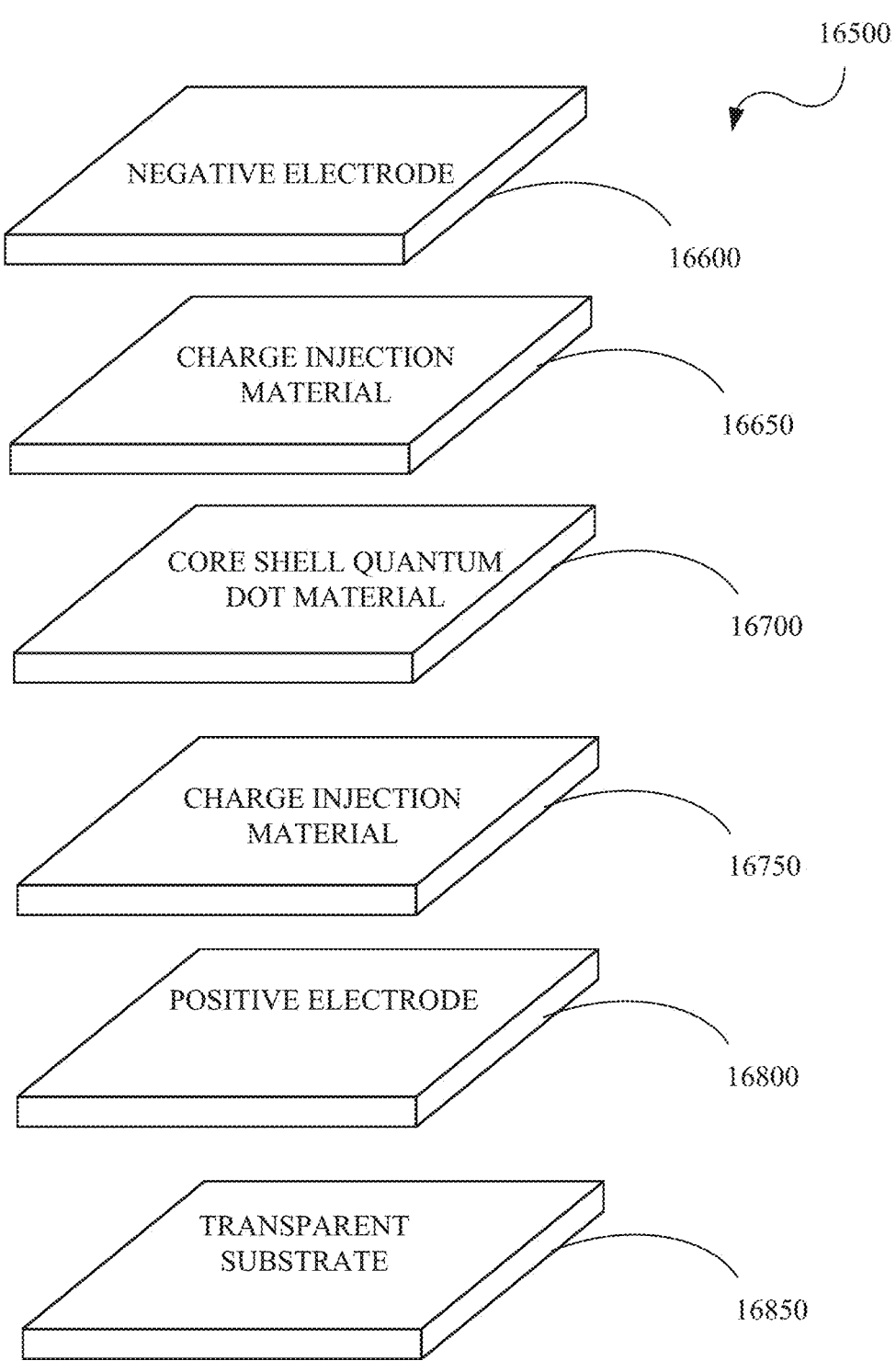

FIGS. 16A and 16B are architectures for quantum dot light emitting diodes (QLEDs). FIG. 16A is a diagram of a quantum dot 16000, which are semiconductor particles with optical and electrical properties in the nanometer size area. The quantum dot 16000, in general, includes a core 16100, a shell 16200 and ligands 16300. The core 16100 are the material emitting colors, the shell 16200 are coatings to protect the core 16100, and the ligands 16300 are long chain molecules so that the quantum dots can be printed in a liquid form.

FIG. 16B is a diagram of a QLED stack 16500 for a vital signs monitoring patch with display in accordance with certain implementations. The QLED stack 16500 includes a negative voltage electrode 16600, a charge injection material layer 16650, a core-shell quantum dot layer 16700, a charge injection layer 16750, a positive voltage electrode 16800, and a transparent substrate 16850. The QLEDs produce pure monochromatic light (red, green, blue) and have low power consumption. Charge injected in the QLED stack 16500 results in electroluminescence. The chemical make-up and size of the quantum dots allows tuning of the color of the emitted light.

In general, a vital signs monitoring patch with integrated display includes a user access layer configured to have at least access to a display section and a first printed silver-silver chloride electrode, a polyethylene foam layer including at least a cut-out for a power supply, where the polyethylene foam layer is arranged to bond to the user access layer, a printed circuit board assembly (PCBA) layer including at least one vital sign monitoring sensor and the power supply, the PCBA layer is connected to the first printed silver-silver chloride electrode and a second printed silver-silver chloride electrode, where the PCBA layer is arranged to bond to the polyethylene foam layer, a sensor layer including reflection mode oximetry measurement components and the second printed silver-silver chloride electrode, a hydrogel based conductive adhesive configured to contact a user surface area, where the hydrogel based conductive adhesive is configured to interact between the user surface area and the second printed silver-silver chloride electrode, a medical tape layer, where the medical tape layer is configured to bond to the user surface area and the sensor layer, and a plunger arranged to operate within a cut-out on the polyethylene foam layer and connected to the PCBA layer, where the plunger is accessible on the user access layer and configured to power on the vital signs monitoring patch with integrated display via the power supply, and where access of the first printed silver-silver chloride electrode by a user completes a circuit with the second printed silver-silver chloride electrode.

In an implementation, the sensor layer is integrated as a bottom surface of the PCBA layer. In an implementation, the first printed silver-silver chloride electrode is printed on a top surface of the PCBA layer. In an implementation, the polyethylene foam layer has a cut-out for first printed silver-silver chloride electrode and has a defined thickness to mitigate inadvertent circuit completion between the first printed silver-silver chloride electrode and the second printed silver-silver chloride electrode. In an implementation, the reflection mode oximetry measurement components further comprising an array of first wavelength light emitting diodes, an array of second wavelength light emitting diodes, and an array of photodiodes, where the array of first wavelength light emitting diodes, the array of second wavelength light emitting diodes, and the array of photodiodes are configured to enable contour mapping of a patch coverage area. In an implementation, the at least one vital signs monitoring sensor is an electrocardiogram (ECG) sensor. In an implementation, the PCBA layer further includes at least one temperature sensor. In an implementation, the PCBA layer further includes a pair of temperature sensors configured to provide a thermal profile of a patch coverage area.

In an implementation, the PCBA layer further includes a pH sensor. In an implementation, the PCBA layer further includes an accelerometer which is configured to detect inclination and fall detection data. In an implementation, the PCBA further includes a wireless component which is configured to transmit at least vital signs data to a vital signs monitoring device. In an implementation, the medical tape layer, the polyethylene foam layer, and the user access layer are arranged and configured to provide bonding and sealing against environmental exposure. In an implementation, the user access layer includes the display section.

In general, a vital signs monitoring patch with integrated display includes a top layer including at least access to a display, a top printed silver-silver chloride electrode and an activation device, a foam layer including at least a cut-out for a power supply and the activation device, where the polyethylene foam layer is arranged to bond to the top layer, a printed circuit board assembly (PCBA) layer having a top surface and a bottom surface, where the top surface including at least an electrocardiogram (ECG) sensor and the power supply, the ECG sensor connected to the first printed silver-silver chloride electrode and a second printed silver-silver chloride electrode, the bottom surface including at least an oximetry sensor and the second printed silver-silver chloride electrode, and the activation device connected to the PCBA layer, a hydrogel based conductive adhesive configured to contact a user skin surface, where the hydrogel based conductive adhesive is configured to interact between a user skin area and the second printed silver-silver chloride electrode, and a contact layer, wherein the contact layer is configured to bond to a user surface area and the bottom surface of the PCBA layer, and where the activation device is configured to power on the vital signs monitoring patch with integrated display via the power supply, and where access of the first printed silver-silver chloride electrode by a user completes a circuit with the second printed silver-silver chloride electrode.

In an implementation, the foam layer has a defined thickness to mitigate inadvertent circuit completion between the first printed silver-silver chloride electrode and the second printed silver-silver chloride electrode. In an implementation, the oximetry sensor further includes an array of first wavelength light emitting diodes, an array of second wavelength light emitting diodes, and an array of photodiodes, where the array of first wavelength light emitting diodes, the array of second wavelength light emitting diodes, and the array of photodiodes are configured to enable contour mapping of a patch coverage area. In an implementation, the PCBA layer further includes at least one temperature sensor, a pH sensor, and an accelerometer. In an implementation, the at least one temperature sensor is a pair of temperature sensors configured to provide a thermal profile of a patch coverage area. In an implementation, the patch includes a rechargeable dock, the rechargeable dock configured to recharge the power supply. In an implementation, the display is a printed display.

In implementations, a vital signs monitoring patch with integrated display includes a multiple layer structure, where a first layer includes a display and access to a first printed silver-silver chloride electrode, a second layer includes at least one vitals sign monitoring component, wherein the first layer is bonded to the second layer, and a third layer includes an oximeter, a second printed silver-silver chloride electrode, and an adhesive for contact with a user surface area, where placement of the second printed silver-silver chloride electrode on the user surface area and access of the first printed silver-silver chloride electrode by a user completes a circuit with the second printed silver-silver chloride electrode when the vital signs monitoring patch with integrated display is powered on.

In implementations, a vital signs monitoring patch with integrated display including an access layer includes a display and access to a first printed silver-silver chloride electrode, at least one middle layer includes at least one vitals sign monitoring component, where one of the at least one middle layer is bonded to the access layer, and another layer includes an oximeter, a second printed silver-silver chloride electrode, and an adhesive for contact with a user surface area, where placement of the second printed silver-silver chloride electrode on the user surface area and access of the first printed silver-silver chloride electrode by a user completes a circuit with the second printed silver-silver chloride electrode when the vital signs monitoring patch with integrated display is powered on.

The construction and arrangement of the methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials and components, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps, and decision steps.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A vital signs monitoring patch with integrated display comprising:
   a multiple layer structure, wherein:
   a first layer includes a display and access to a first printed silver-silver chloride electrode;
   a second layer includes at least one vitals sign monitoring component, wherein the first layer is bonded to the second layer;
   a third layer includes an oximeter, a second printed silver-silver chloride electrode, and an adhesive for contact with a user surface area; and a fourth layer comprises a foam spacer to mitigate inadvertent circuit completion between the first printed silver-silver chloride electrode and the second printed silver-silver chloride electrode, wherein placement of the second printed silver-silver chloride electrode on the user surface area and access of the first printed silver-silver chloride electrode by a user completes a circuit with the second printed silver-silver chloride electrode when the vital signs monitoring patch with integrated display is powered on.

2. The patch of claim 1, wherein the third layer is integrated as a bottom surface of the second layer.

3. The patch of claim 2, wherein the first printed silver-silver chloride electrode is printed on a top surface of the second layer.

4. The patch of claim 3, wherein the foam spacer of the fourth layer has a cut-out for the first printed silver-silver chloride electrode and has a defined thickness.

5. The patch of claim 1, wherein the oximeter is a reflection mode oximeter.

6. The patch of claim 1, wherein the oximeter further comprises:

an array of first wavelength light emitting diodes;
an array of second wavelength light emitting diodes; and
an array of photodiodes,
wherein the array of first wavelength light emitting diodes, the array of second wavelength light emitting diodes, and the array of photodiodes are configured to enable contour mapping of a patch coverage area to determine physiological parameters at different points relative to the patch coverage area.

7. The patch of claim 6, wherein the at least one vitals sign monitoring component is an electrocardiogram (ECG) sensor.

8. The patch of claim 7, wherein the second layer further includes at least one temperature sensor.

9. The patch of claim 7, wherein the second layer further includes a pair of temperature sensors configured to provide a thermal profile of a patch coverage area.

10. The patch of claim 9, wherein the second layer further includes a potentiometric pH sensor.

11. The patch of claim 10, wherein the second layer further includes an accelerometer which is configured to detect inclination and fall detection data.

12. The patch of claim 1, wherein the second layer further includes a wireless component which is configured to transmit at least vital signs data to a vital signs monitoring device.

13. The patch of claim 1, wherein the multiple layer structure includes one or more attachment layers configured to provide bonding and sealing against environmental exposure.

14. A vital signs monitoring patch with integrated display comprising:

an access layer includes a display and access to a first printed silver-silver chloride electrode;
at least one middle layer includes at least one vitals sign monitoring component, wherein one of the at least one middle layer is bonded to the access layer; and
another layer includes an oximeter, a second printed silver-silver chloride electrode, and an adhesive for contact with a user surface area,
wherein placement of the second printed silver-silver chloride electrode on the user surface area and access of the first printed silver-silver chloride electrode by a user completes a circuit with the second printed silver-silver chloride electrode when the vital signs monitoring patch with integrated display is powered on.

15. The patch of claim 14, wherein another one of the at least one middle layer has a defined thickness to mitigate inadvertent circuit completion between the first printed silver-silver chloride electrode and the second printed silver-silver chloride electrode.

16. The patch of claim 14, wherein the oximeter further comprises:

an array of first wavelength light emitting diodes;
an array of second wavelength light emitting diodes; and
an array of photodiodes,
wherein the array of first wavelength light emitting diodes, the array of second wavelength light emitting diodes, and the array of photodiodes are configured to enable contour mapping of a patch coverage area to determine physiological parameters at different points relative to the patch coverage area.

17. The patch of claim 16, wherein the at least one middle layer further includes at least one temperature sensor, a pH sensor, and an accelerometer.

18. The patch of claim 17, wherein the at least one temperature sensor is a pair of temperature sensors configured to provide a thermal profile of a patch coverage area.

19. The patch of claim 14, further comprising:

a rechargeable dock, the rechargeable dock configured to recharge a power supply.

20. The patch of claim 14, wherein some of the at least one middle layer includes one or more attachment layers configured to provide bonding and sealing against environmental exposure.

* * * * *